(12) United States Patent
Squirrell et al.

(10) Patent No.: US 6,265,177 B1
(45) Date of Patent: Jul. 24, 2001

(54) ENZYME ASSAY FOR MUTANT FIREFLY LUCIFERASE

(75) Inventors: David James Squirrell, Salisbury; Peter John White, Cambridge; Christopher Robin Lowe, Cambridge; James Augustus Henry Murray, Cambridge, all of (GB)

(73) Assignee: The United States of America as represented by the Secretary of the State of Defence, Washington, DC (US)

( * ) Notice: Subject to any disclaimer, the term of this patent is extended or adjusted under 35 U.S.C. 154(b) by 0 days.

(21) Appl. No.: 09/380,061

(22) PCT Filed: Apr. 7, 1998

(86) PCT No.: PCT/GB98/01026

§ 371 Date: Aug. 25, 1999

§ 102(e) Date: Aug. 25, 1999

(87) PCT Pub. No.: WO98/46729

PCT Pub. Date: Oct. 22, 1998

(30) Foreign Application Priority Data

Apr. 11, 1997 (GB) .................................................. 9707486

(51) Int. Cl.[7] .............................. C12Q 1/66; C12N 9/02; C12N 1/21; C12N 15/52; C07H 21/04
(52) U.S. Cl. .......................... 435/8; 435/189; 435/252.3; 435/320.1; 435/440; 435/810; 536/23.2
(58) Field of Search ................................ 435/189, 320.1, 435/252.3, 810, 440; 536/23.2

(56) References Cited

U.S. PATENT DOCUMENTS 5,196,524   3/1993   Gustafson et al. ................... 536/23.2

FOREIGN PATENT DOCUMENTS

| 0 449 621 | 10/1991 | (EP) . |
|---|---|---|
| WO 95 18853 | 7/1995 | (WO) . |
| WO 95 25798 | 9/1995 | (WO) . |
| WO 96 22376 | 7/1996 | (WO) . |

OTHER PUBLICATIONS

Dementieva et al, "Physicochemical properties of recombinant Luciola mingrelica luciferace and its mutant forms" *Biochemistry*, vol. 61, No. 1, 1996, pp. 115–119.

Dementieva et al, "Assay of ATP in intact *Escherichia coli* cells expressing recombinant firefly luciferace" *Biochemistry*, vol. 61, No. 7, 1996, pp. 915–920.

Liu et al, "Factors influencing the efficiency of cationic liposome–mediated intravenous gene delivery", *Nature Biotechnology*, vol. 15, 1997, pp. 167–173.

*Primary Examiner*—Elizabeth Slobodyansky
(74) *Attorney, Agent, or Firm*—Nixon & Vanderhye P.C.

(57) ABSTRACT

Enzymes and methods suitable for assaying ATP, and specific application for such assays are described and claimed. In particular, there is described a recombinant mutant luciferase having a mutation for example, in the amino-acid corresponding to amino acid residue number 245 in *Photinus pyralis*, is such that the $K_m$ for ATP of the luciferase is increased e.g. five-fold with respect to that of the corresponding non-mutated enzyme such that it is of the order of 500 μm–1 mM. Also disclosed are luciferases having additional mutations conferring improved thermostability or altered wavelength of emitted light. Recombinant polynucleotides, vectors and host cells are also disclosed, as are methods of assaying the amount of ATP in a material (e.g. cells) optionally in real-time. Also disclosed are test-kits for in vitro assays.

34 Claims, 9 Drawing Sheets

Fig. 2.
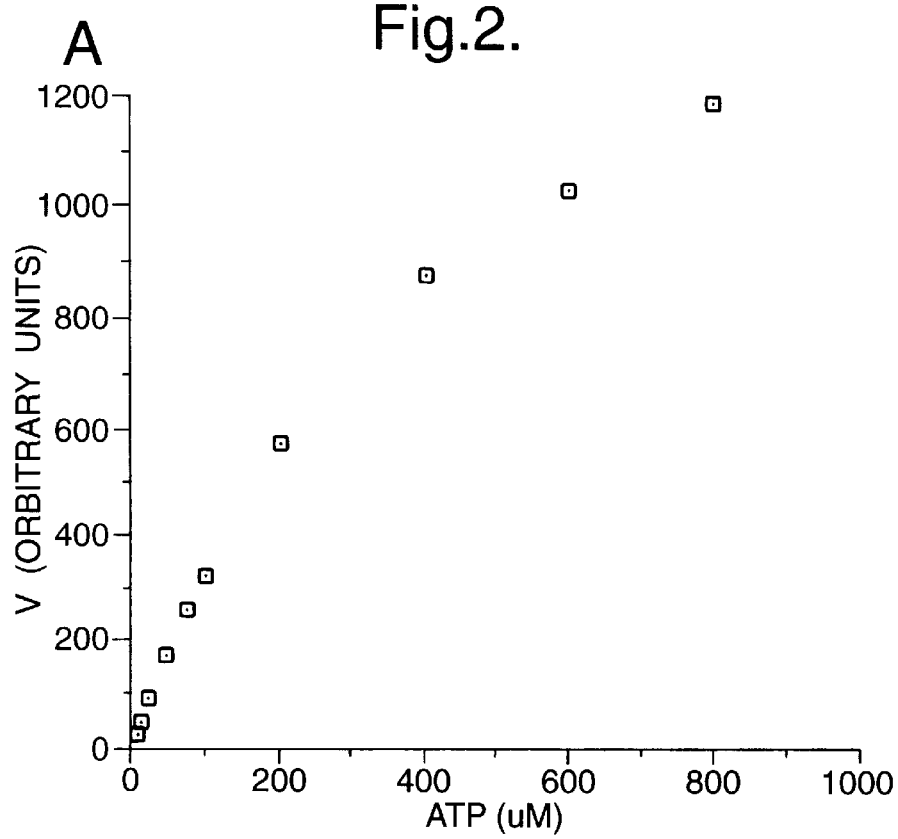
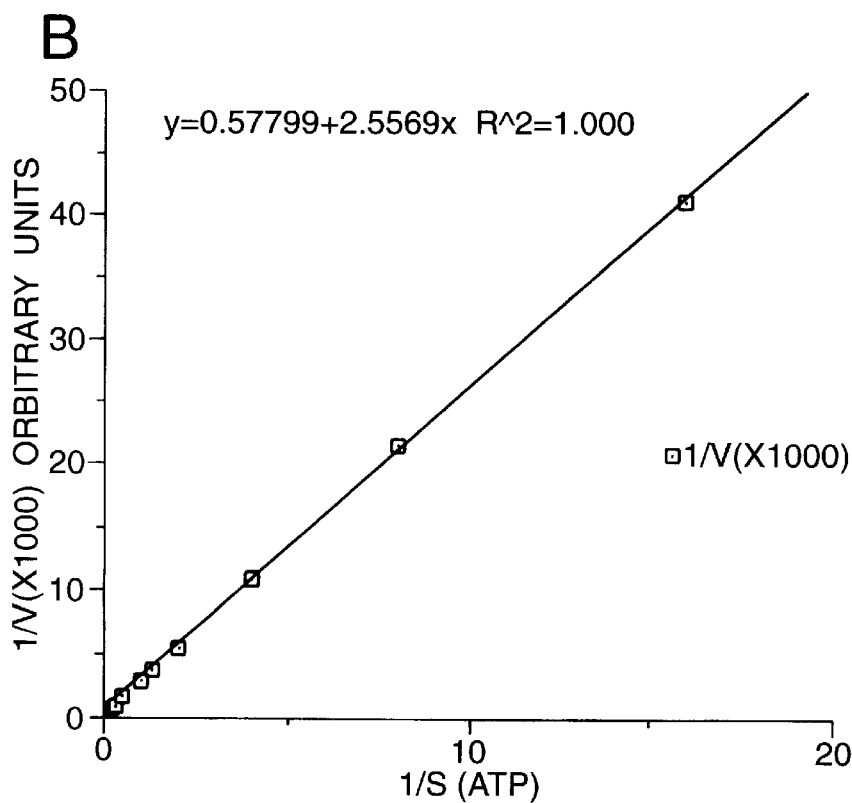

Fig.3.

```
         H245
          ↓
Pp  230→ I I P D T A I L S V V P F H H G F G M F T T L G Y L I C
         o   o o                 o o o o o o o o o o o o o
Lc       V S P G T A V L T V V P F H H G F G M F T T L G Y L I C
                           ↑
                          247                              23/28 identical P318A
          ↓
Pp  301→ I D K Y D L S N L H E I A S G G A P L S K E V G E A V A K R F H L P G
             o o o o o o o o   o o o o o o o o o o o o o o o o   o o o o o
Lc       L N K Y D L S N L V E I A S G G A P L S K E V G E A V A R R F H L P G
         ↑
        303                        ↑
                                  320                              30/35 identical S347T
          ↓
Pp  330→ R F H L P G I R Q G Y G L T E T T S A I L I T P E G D D K P G A V G K V V P F F
         o o   o o o   o o o o o o o o o o o   o o o o o o o o o o   o o o o   o
Lc       R F N L P G V R Q G Y G L T E T T S A I I I T P E G D D K P G A S G K V V P L F
         ↑                                 ↑
        332                               349                             35/40 identical
```

(2) INFORMATION FOR SEQ ID NO:1:

(i) SEQUENCE CHARACTERISTICS:
        (A) LENGTH: 1722 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
        (A) ORGANISM: Photinus pyralis (ix) FEATURE:
        (A) NAME/KEY: CDS
        (B) LOCATION: 4..1653

(xi) SEQUENCE DESCRIPTION: SEQ ID NO:1:

```
CAAATGGAAG ACGCCAAAAA CATAAAGAAA GGCCCGGCGC CATTCTATCC TCTAGAGGAT     60

GGAACCGCTG GAGAGCAACT GCATAAGGCT ATGAAGAGAT ACGCCCTGGT TCCTGGAACA    120

ATTGCTTTTA CAGATGCACA TATCGAGGTG AACATCACGT ACGCGGAATA CTTCGAAATG    180

TCCGTTCGGT TGGCAGAAGC TATGAAACGA TATGGGCTGA ATACAAATCA CAGAATCGTC    240

GTATGCAGTG AAAACTCTCT TCAATTCTTT ATGCCGGTGT TGGGCGCGTT ATTTATCGGA    300

GTTGCAGTTG CGCCCGCGAA CGACATTTAT AATGAACGTG AATTGCTCAA CAGTATGAAC    360

ATTTCGCAGC CTACCGTAGT GTTTGTTTCC AAAAAGGGGT TGCAAAAAAT TTTGAACGTG    420

CAAAAAAAAT TACCAATAAT CCAGAAAATT ATTATCATGG ATTCTAAAAC GGATTACCAG    480

GGATTTCAGT CGATGTACAC GTTCGTCACA TCTCATCTAC CTCCCGGTTT TAATGAATAC    540

GATTTTGTAC CAGAGTCCTT TGATCGTGAC AAAACAATTG CACTGATAAT GAATTCCTCT    600

GGATCTACTG GGTTACCTAA GGGTGTGGCC CTTCCGCATA GAACTGCCTG CGTCAGATTC    660

TCGCATGCCA GAGATCCTAT TTTTGGCAAT CAAATCATTC CGGATACTGC GATTTTAAGT    720
```

Fig.6B.

```
GTTGTTCCAT TCCATCACGG TTTTGGAATG TTTACTACAC TCGGATATTT GATATGTGGA    780
TTTCGAGTCG TCTTAATGTA TAGATTTGAA GAAGAGCTGT TTTTACGATC CCTTCAGGAT    840
TACAAAATTC AAAGTGCGTT GCTAGTACCA ACCCTATTTT CATTCTTCGC CAAAAGCACT    900
CTGATTGACA AATACGATTT ATCTAATTTA CACGAAATTG CTTCTGGGGG CGCACCTCTT    960
TCGAAAGAAG TCGGGGAAGC GGTTGCAAAA CGCTTCCATC TTCCAGGGAT ACGACAAGGA   1020
TATGGGCTCA CTGAGACTAC ATCAGCTATT CTGATTACAC CCGAGGGGGA TGATAAACCG   1080
GGCGCGGTCG GTAAAGTTGT TCCATTTTTT GAAGCGAAGG TTGTGGATCT GGATACCGGG   1140
AAAACGCTGG GCGTTAATCA GAGAGGCGAA TTATGTGTCA GAGGACCTAT GATTATGTCC   1200
GGTTATGTAA ACAATCCGGA AGCGACCAAC GCCTTGATTG ACAAGGATGG ATGGCTACAT   1260
TCTGGAGACA TAGCTTACTG GGACGAAGAC GAACACTTCT TCATAGTTGA CCGCTTGAAG   1320
TCTTTAATTA AATACAAAGG ATATCAGGTG GCCCCGCTG AATTGGAATC GATATTGTTA    1380
CAACACCCCA ACATCTTCGA CGCGGGCGTG GCAGGTCTTC CCGACGATGA CGCCGGTGAA   1440
CTTCCCGCCG CCGTTGTTGT TTTGGAGCAC GGAAAGACGA TGACGGAAAA AGAGATCGTG   1500
GATTACGTCG CCAGTCAAGT AACAACCGCG AAAAAGTTGC GCGGAGGAGT TGTGTTTGTG   1560
GACGAAGTAC CGAAAGGTCT TACCGGAAAA CTCGACGCAA GAAAAATCAG AGAGATCCTC   1620
ATAAAGGCCA GAAGGGCGG AAAGTCCAAA TTGTAAAATG TAACTGTATT CAGCGATGAC   1680
GAAATTCTTA GCTATTGTAA TCCTCCGAGG CCTCGAGGTC GA                     1722
```

Fig.7.

MUTAGENIC OLIGONUCLEOTIDES

Sequence ID No. 2

H245A:

```
              736 737        744
               ↓↓             ↓
5'- GTT GTT CCA TTC CAT gcC GGT TTc GGA ATG TTT AC-3'
```

Sequence ID No. 3

H245Q:

```
                   738        744
                    ↓          ↓
5'- GTT GTT CCA TTC CAT CAg GGT TTc GGA ATG TTT AC-3'
```

Sequence ID No. 4

H245N:

```
                  736        744
                   ↓          ↓
5'- GTT GTT CCA TTC CAT aAC GGT TTc GGA ATG TTT AC-3'
```

Sequence ID No. 5

WILD TYPE SEQUENCE:

```
   721                H245                              nt 753
    ↓                 | |                                 ↓
5'- GTT GTT CCA TTC CAT CAC GGT TTT GGA ATG TTT AC-3'
```

```
                                         CAA
nt numbering is from luc gene sequence,   |  ....
                                         nt 1
```

(2) INFORMATION FOR SEQ ID NO:6:

(i) SEQUENCE CHARACTERISTICS:
      (A) LENGTH: 550 amino acids
      (B) TYPE: amino acid
      (C) STRANDEDNESS: single
      (D) TOPOLOGY: unknown

Fig.8A.

(ii) MOLECULE TYPE: protein (iii) HYPOTHETICAL: NO (vi) ORIGINAL SOURCE:
       (A) ORGANISM: Photinus pyralis (ix) FEATURE:
       (A) NAME/KEY: Modified-site
       (B) LOCATION: 245

(xi) SEQUENCE DESCRIPTION: SEQ ID NO:6:

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asn Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
            115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
    210                 215                 220
```

Fig.8B.

```
Pro Ile Phe Gly Asn Gln Ile Ile Pro Asp Thr Ala Ile Leu Ser Val
225             230             235             240
Val Pro Phe His Gln Gly Phe Gly Met Phe Thr Thr Leu Gly Tyr Leu
            245             250             255
Ile Cys Gly Phe Arg Val Val Leu Met Tyr Arg Phe Glu Glu Glu Leu
            260             265             270
Phe Leu Arg Ser Leu Gln Asp Tyr Lys Ile Gln Ser Ala Leu Leu Val
            275             280             285
Pro Thr Leu Phe Ser Phe Phe Ala Lys Ser Thr Leu Ile Asp Lys Tyr
    290             295             300
Asp Leu Ser Asn Leu His Glu Ile Ala Ser Gly Gly Ala Pro Leu Ser
305             310             315             320
Lys Glu Val Gly Glu Ala Val Ala Lys Arg Phe His Leu Pro Gly Ile
            325             330             335
Arg Gln Gly Tyr Gly Leu Thr Glu Thr Thr Ser Ala Ile Leu Ile Thr
            340             345             350
Pro Glu Gly Asp Asp Lys Pro Gly Ala Val Gly Lys Val Val Pro Phe
            355             360             365
Phe Glu Ala Lys Val Val Asp Leu Asp Thr Gly Lys Thr Leu Gly Val
    370             375             380
Asn Gln Arg Gly Glu Leu Cys Val Arg Gly Pro Met Ile Met Ser Gly
385             390             395             400
Tyr Val Asn Asn Pro Glu Ala Thr Asn Ala Leu Ile Asp Lys Asp Gly
            405             410             415
Trp Leu His Ser Gly Asp Ile Ala Tyr Trp Asp Glu Asp Glu His Phe
            420             425             430
Phe Ile Val Asp Arg Leu Lys Ser Leu Ile Lys Tyr Lys Gly Tyr Gln
    435             440             445
Val Ala Pro Ala Glu Leu Glu Ser Ile Leu Leu Gln His Pro Asn Ile
    450             455             460
Phe Asp Ala Gly Val Ala Gly Leu Pro Asp Asp Asp Ala Gly Glu Leu
465             470             475             480
Pro Ala Ala Val Val Val Leu Glu His Gly Lys Thr Met Thr Glu Lys
            485             490             495
Glu Ile Val Asp Tyr Val Ala Ser Gln Val Thr Thr Ala Lys Lys Leu
            500             505             510
Arg Gly Gly Val Val Phe Val Asp Glu Val Pro Lys Gly Leu Thr Gly
    515             520             525
Lys Leu Asp Ala Arg Lys Ile Arg Glu Ile Leu Ile Lys Ala Lys Lys
    530             535             540
Gly Gly Lys Ser Lys Leu
545             550
```

ENZYME ASSAY FOR MUTANT FIREFLY LUCIFERASE

TECHNICAL FIELD

The present invention relates broadly to enzymes and methods suitable for assaying ATP. It further relates to specific applications for such assays.

BACKGROUND ART

Intracellular ATP concentrations can vary 10-fold or more depending upon a cell's state of health or developmental stage. It is of great value to be able to measure fluctuations in intracellular ATP levels as a means of investigating e.g. the effects of drugs, toxins, hormones, environmental agents or disease on cells.

There is apparently at present no convenient method for analysing the concentration of ATP in vivo. For instance, in Dementieva et al (1996) Biochemistry (Moscow) Vol 61, No. 7., the intracellular concentration of ATP was measured in E. coli by calculating the total amount of ATP present using a recombinant luciferase, and dividing by an estimated total cell volume.

Such an indirect approach can at best produce only an estimate of the actual ATP concentration.

The measurement of ATP concentration in cells has also been performed using an in vitro coupled assay, such as that disclosed in the Sigma Diagnostic Kit Catalog No. 366, in which Phosphoglycerate kinase is used to convert 3-phosphoglycerate to 1,3 diphosphoglycerate in an [ATP]-dependent fashion. The 1,3 diphosphoglycerate is then converted to glyceraldehyde-3-P concommitantly with conversion of NADH to NAD, which can be monitored spectroscopically. The assay has a dynamic range up to 1 mM; the expected range is 380–620 $\mu$m when used with blood cells.

However it can be seen that, as with all coupled assays, the test is inevitably cumbersome to perform. Additionally it could not readily be adapted for in vivo use. It would thus be a contribution to the art to provide materials and methods which overcome some of the drawbacks of the prior art.

DISCLOSURE OF THE INVENTION

In a first aspect of the invention there is provided a recombinant mutant luciferase having a mutation which is such that the $K_m$ for ATP of the luciferase is increased with respect to that of the corresponding non-mutated enzyme. Preferably the $K_m$ is at least double that of the non-mutated enzyme, and more preferably at least around five, ten, or twenty times higher than that of the non-mutated enzyme.

Luciferases are, of course, already known in the art. In the presence of $Mg^{2+}$, luciferase (originally obtained from fireflies) catalyzes the reaction of luciferin, ATP and $O_2$ to form oxyluciferin, AMP, $CO_2$, pyrophosphate and light. This basic property (luciferin and ATP to produce light) is hereinafter referred to as 'luciferase activity'.

The term 'luciferase' as used in relation to the invention is intended to embrace all luciferases, or recombinant enzymes derived from luciferases which have luciferase activity. This explicitly includes recombinant mutant luciferases which have deletions, additions or substitutions to their amino acid structure provided that they retain luciferase activity. Such luciferases will typically have considerable homology (e.g. up to 70, 80, 90, or 99%) with wild-type enzymes. However the crucial technical feature of the luciferases of the present invention which distinguishes them from those of the prior art is that they have a mutation which causes an increase in the $K_m$ for ATP of the luciferase as compared with that measured for a corresponding enzyme which differs only in it that it lacks that same mutation.

This increase $K_m$ may be measured by the person of ordinary skill in the art by conventional enzyme assays, as described in more detail in the Examples below.

It should be noted that in the prior art, luciferase has sometimes been used as a marker for gene expression (in vivo) where its production in a cell is linked to a particular genetic control element. Luciferin is added exogenously and intracellular ATP concentrations, under almost all conditions, will be such that the enzyme is saturated. Thus the switching on of gene expression is signalled by light that is emitted in a quantitative manner according to the amount of active luciferase that is generated.

However it should be stressed that in the previously known systems it is generally the concentration of luciferase which is measured; this concentration is then correlated with a different event e.g. the efficiency of a promoter. Indeed it has, on occasions, been an object of the prior art teaching on luciferases to reduce the $K_m$ for ATP see e.g. WO 96/22376) which ensures that changes in the ambient [ATP] does not interfere with the assay.

Similarly the assay disclosed by Dementieva et al (1996) discussed above requires that all of the ATP be efficiently converted to light so that the total ATP present can be calculated. This approach requires a low $K_m$ luciferase so that the enzyme operates at near maximal velocity until all the ATP is hydrolysed.

By making available luciferases which have an increased $K_m$ compared with those already known in the art, the present inventors have for the first time opened up the possibility of using these enzymes to measure steady state ATP concentrations over range which was previously unsuitable. This is because, generally speaking, the relationship between enzyme velocity (V, as measured by light intensity) and substrate concentration (of ATP, where luciferin is in excess) is as follows:

$$V=V_m[ATP]/K_m+[ATP]$$

It can therefore be seen that only when the $K_m$ is greater than (or of a similar order as) the ambient [ATP] will there be a degree of proportionality between changes in [ATP] and changes in light intensity. Where the $K_m$ is much less than the ambient [ATP], any changes in [ATP] will not tangibly effect the measured light intensity. Clearly the more sensitive the light detection is, the smaller the measurable changes in 'V' can be, and the smaller the $K_m$ can be with respect to the [ATP] range being assessed.

For certain applications, e.g. in vivo measurements, it may be advantageous to have a luciferase wherein the $K_m$ is of the order of between 400 $\mu$m to 1.4 mM e.g. 500 $\mu$m, 600 $\mu$m, 1 mM etc. However, as can be appreciated from the discussion above, the main criterion is that the $K_m$ is not much less than the expected [ATP] range to be assessed, and the phrase 'of the order of' should be construed accordingly.

A particular expected [ATP] range which is important for physiological assays of blood cells is between 300 $\mu$m and 1 mM, or more particularly 380 $\mu$m and 620 $\mu$m, (cf. Sigma Diagnostic Kit, Catalog No. 366 discussed above). For other mammalian cells such as hepatocytes, the [ATP] range is 2.5 mM–6 mM (see Dementieva et al (1996) discussed above. Use of the recombinant luciferases of the present invention for continuous assays in these ranges is particularly envisaged.

The disclosure of the present application makes such high $K_m$ luciferases available for the first time. The prior art disclosures reveal only luciferases having a $K_m$ of between 60 μm and 150 μm, which would be saturated in these ranges.

It is also advantageous, as with all enzymes used in assays, that the mutant enzyme retains sufficient activity (i.e. a high maximum turnover number, giving a high $V_m$) such that practical concentrations of enzyme can give detectable results.

Preferably the activity for ATP of the mutant is at least 5–100% of that of the corresponding wild-type; however reduced-activity as a result of the high $K_m$ mutation can, if necessary, be compensated for by using more enzyme or more sensitive detection if required.

In one embodiment of the first aspect there is disclosed a luciferase wherein the amino-acid corresponding to amino acid residue number 245 in *Photinus pyralis* has been substituted with respect to the corresponding wild-type amino acid residue such that the $K_m$ for ATP is increased with respect to that of the corresponding non-mutated enzyme.

It should be noted that the sequences of a number of luciferases from different sources have already been published in the literature see e.g. WO 95/25798 for *P pyralis* (SEQ ID NOs:1, and 21); EP 0 524 448 for *Luciola cruciata* (SEQ ID NOs:13 and 14) and *Luciola lateralis* (SEQ ID NOs:15 and 16). Other known luc genes include *Luciola mingrelica* (SEQ ID NOs:17 and 18), and *Lampyris noctiluca* (SEQ ID NOs:19 and 20) (see Newby et al (1996) Biochemical J 313: 761–767.)

Whether an amino-acid in a luciferase 'corresponds' to number 245 in *P pyralis* (which is His in the wild-type, non-mutated enzyme) can be established by the person of ordinary skill in the art without difficulty as follows: the sequence of the luciferase is established (either from the literature or by sequencing); the sequence is aligned with *P pyralis*, for instance using commercially available software (e.g. "Bestfit" from the University of Wisconsin Genetics Computer Group; see Devereux et al (1984) Nucleic Acid Research 12: 387–395) or manually such as to demonstrate maximal homology and align conserved amino acids; the amino acid corresponding to number 245 in *P pyralis* is identified. An example of this is shown below using *L cruciata*—the corresponding acid in that case is number 247.

Once identified a mutant can be prepared e.g. by site directed mutagenesis by methods commonly used in the art and exemplified below.

Preferably corresponding amino-acid is substituted for an uncharged amino acid, for instance nonpolar (e.g. Ala) or uncharged polar (e.g. Asn, or Gln):

| CLASS | EXAMPLES OF AMINO ACID |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His |

It should be noted that WO 95/18853 (PROMEGA) lists a large number (over 80) of *Pyrophorus plagiophtalamus* mutants which are reported to have altered spectral properties. However the $K_m$ for ATP of the mutants is not reported, nor indeed discussed at any point in the application.

In another embodiment of the first aspect there is disclosed a luciferase wherein the amino-acid corresponding to amino acid residue number 318 in *Photinus pyralis* has been substituted with respect to the corresponding wild-type amino acid residue such that the $K_m$ for ATP is increased with respect to that of the corresponding non-mutated enzyme. Correspondence may be assessed as above; preferably the amino acid (Ser in the wild type) is substituted for a bulkier one (e.g. Thr).

In preferred forms the mutant luciferases of the present invention incorporate one or more further mutations capable of conferring one or more of the following properties with respect to a corresponding non-mutated enzyme: improved thermostability; altered wavelength of emitted light. Some suitable mutations are already known to those skilled in the art; see e.g. WO 95/25798 and WO 96/22376 and EP 0 524 448 for thermostability improving mutations (e.g. at positions corresponding to 354 and 215 of *P pyralis*).

Preferably the mutation causing the increased $K_m$ itself improves one or more of these properties, particularly thermostability. It should be noted that an enhanced stability at around 37° C. is especially advantageous for enzymes which are to be employed in vivo.

In a further embodiment the luciferases may be in the form of fusion proteins or incorporate polypeptide extensions. This may improve the ease by which they can be produced, localised in vivo or extracted and purified.

In a second aspect of the invention there is disclosed a recombinant polynucleotide encoding a mutant luciferase of the present invention, as described above.

In a third aspect there are disclosed vectors comprising a polynucleotide of the second aspect. For instance vectors further comprising a replication element which permits replication of the vector in a suitable host cell and/or a promoter element which permits expression of said polynucleotide in a suitable host cell. The promoter may be a constitutive promoter. Optionally the promoter element may be tissue- or organ-specific.

In a fourth aspect there is disclosed a host cell containing, or transformed with, a vector of the third aspect.

Optionally the host cell of the fourth aspect may express one or more further luciferases which have a lower $K_m$ for ATP than those of the present invention, and possibly emit light of a different wavelength, such as to extend the useful range of any assay, and/or allow the use of a ratiometric assay i.e. one in which the activity of the high $K_m$ mutant is compared with that of a further luciferase. The further luciferases may be recombinant non-mutant luciferases or recombinant mutant luciferases having a mutation which is such that the $K_m$ for ATP of the luciferase is decreased with respect to that of the corresponding non-mutated enzyme (see e.g. WO 96/22376.

Coloured mutants are disclosed in WO 95/18853 and in Ohmiya et al (1996) FEBS Letters 384: 83–86.

In a fifth aspect there is disclosed a process for producing a luciferase of the present invention comprising culturing a host cell as described in the fourth aspect.

In a sixth aspect there is disclosed a single cell organism consisting of a host cell as described above, or a multicellular organ or organism comprising it. The use of e.g. transgenic higher animals in which the luciferases of the present invention are expressed could allow in vivo study of [ATP] in different types of cell or tissue as described in more detail below. In particular, as ATP is present in virtually all living cells, any type of cell into which luciferase could be cloned, from bacterial to plant or animal, could be studied through the measurement of ATP changes.

Thus in a seventh aspect of invention there is disclosed a method of assaying the amount of ATP in a material comprising use of a recombinant luciferase as described above.

Preferably the method comprises the following steps (a) the luciferase is contacted with the material and luciferin; (b) the intensity of light emitted by the luciferase is measured; and (c) the measurement in step (b) is correlated with the amount of ATP in the material.

The measurement in step (b) may be compared with a control value such as minimise base-line errors.

The assay can be in vitro or in vivo.

More preferably the material itself is a cell, in to which the luciferase is introduced e.g. by transforming the cell with a vector as described above. Alternatively the luciferase may be introduced into the cell by direct injection.

Equally the material measured may be part of a synapse i.e. the ATP is neurotransmitter.

Generally the assay will be most useful for real-time analysis (on a time-scale of seconds e.g. using a CCD camera, photomultiplier or photodiode) of events initiated by particular stimuli (e.g. addition of an active agent to the material). In this case the assay can monitor changes in [ATP] concentration over a relatively short time-scale. Such measurement will not, therefore, be greatly affected by longer time-scale events, such as changes in the concentration of luciferase in the system. These changes can be correlated with cellular events e.g. tissue necrosis may be associated with falling [ATP], fatigue in muscle likewise. Such continuous assays have hitherto not been possible.

Other possible applications include measuring the effect of drug treatments on various tissues; toxins and uncoupling agents on oxidative phosphorylation; bacterial infection; metabolic processes and stress (e.g. obesity and exercise); studies of brain activity (e.g. memory function and mental disorders) etc.

If appropriate the [ATP] can be measured periodically (rather than constantly) using photographic film.

Essentially the monitoring can be done in ways analogous to those already used in the art for other applications e.g. for the photonic detection of bacterial pathogens in living hosts disclosed by Contag et al (1995) Molecular Microbiology 18(4): 593–603. In that paper a Hamamatsu intensified CCD camera was used to visualise Salmonella Typhimurium expressing luciferase during infection of a mouse. Equally a system equivalent to PET (positron emission tomography—as used in brain scans) could be used to achieve precise localisation of luciferase-generated light to allow the metabolism of specific body regions to be ascertained.

Generally speaking it will be necessary to introduce luciferin into the system being studied. By 'luciferin' is meant any co-factor which has luciferin activity i.e. can be used in conjunction with luciferase to cause light to be emitted in the presence of ATP. The manner by which this is introduced in to the system will depend on the system itself. For instance where animal cells are being studied, luciferin may be introduced by ingestion of luciferin or a precursor thereof by an animal of which the cell is a constituent part. Similarly when the system being studied is one or more plant cells, the luciferin may simply be introduced into the cell by applying a solution of luciferin or a precursor thereof to a plant of which the cell is a constituent part.

In a final aspect of the invention there is disclosed a test kit comprising a luciferase discussed above and further comprising one or more of the following(a) a buffer or dry materials for preparing a buffer; (b) ATP standards; (c) luciferin; (d) Dithiothreitol (e) instructions for carrying out an ATP assay.

The invention will now be further described with reference to the following none-limiting Figures, Sequence Listings and Examples.

Figures

FIG. 1. shows plasmid pPW601a as described in Example 1.

FIG. 2. for mutant H245A, (a) shows the plot of V against [ATP] and (b) shows 1/V against 1/[ATP] as described in Example 1.

FIG. 3. shows a sequence comparison of one region of $P$ $pyralis$ (Pp) (SEQ ID NOs: 7, 9 and 11, respectively) and the corresponding region of $L$ $cruciata$ (Lc) (SEQ ID NOs:8, 10 and 12, respectively as described in Example 2.

FIG. 4 is a graph showing light emission versus ATP concentration for mutant H245N.

FIG. 5 . shows the effect of the addition of nutrient broth to luciferase-expressing $E$. $coli$ cells pre-charged with Luciferin as described in Example 6.

FIGS. 6A and 6B show SEQ ID NO:1 which is the nucleotide sequence of the wild type luc gene from $P$ $pyralis$.

FIG. 7 shows Seq ID Nos. 2–5 which are the primers used to create the mutations H245A, N and Q (Ala, Asn, or Gln—see Seq ID Nos. 2, 3 & 4) and the equivalent wild-type sequence (Seq ID No 5).

FIGS. 8A and 8B shows SEQ ID NO:6 which is the amino acid sequence of a high $K_m$ mutant H245Q of the present invention, wherein amino acid 245 has been changed to Gln.

EXAMPLES

EXAMPLE 1

Production of Recombinant High $K_m$ Mutant Luciferase

Except where otherwise stated, the methods employed were as those used by White et al (1996) Biochemical Journal 319: 342–350, which is concerned with thermostable mutants.

Figure 1:
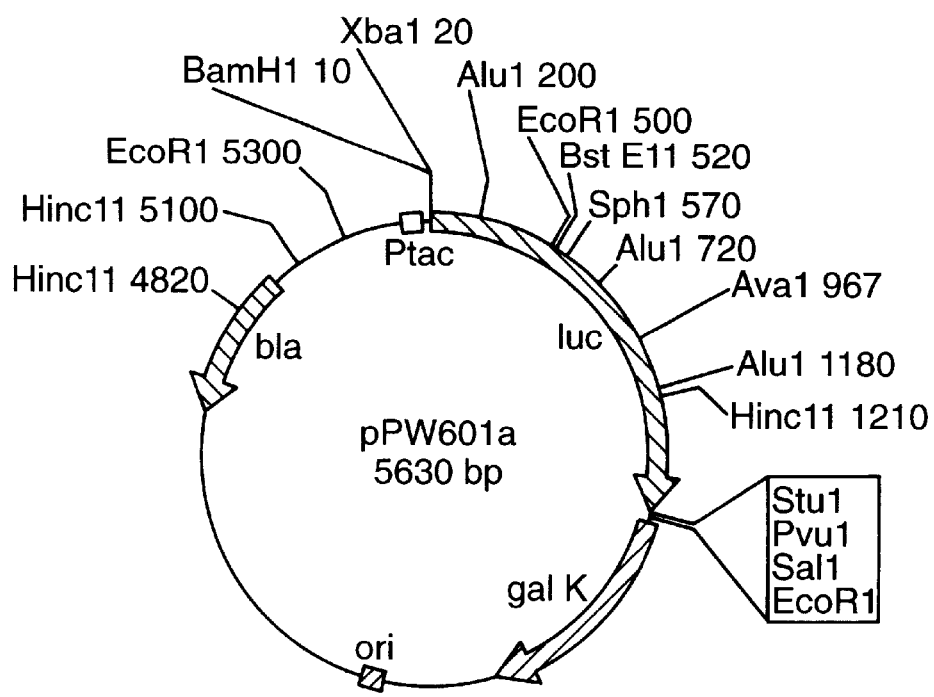

STARTING MATERIALS: Mutants were generated by site directed mutagenesis of the plasmid pPW601a (FIG. 1) comprising the luciferase gene, luc, from $P$ $pyralis$. The wild type luc gene from $P$ $pyralis$ is shown at Seq ID No. 1. Plasmid pPW601a was created by cloning the luc gene BamHI/SstI fragment from pGEM-luc (available from Promega) into pDR540 (available from Pharmacia). The unique XhoI site in the polylinker of the plasmid was removed to simplify the following procedures.

SITE DIRECTED MUTAGENESIS: Three mutagenic oligonucleotides were used to create the mutations H245A, N and Q (Ala, Asn, or Gln—see Seq ID Nos. 2, 3 & 4). The equivalent wild-type sequence is shown at Seq ID No. 5. The oligonucleotides also introduced a silent mutation which destroys a unique Xmn I site in the luc gene—this did not result in an amino acid substitution but facilitated mutant selection. The mutagenesis was carried out in accordance with the kit instructions of kit supplied by Clontech laboratories Inc, Palo Alto, Calif. USA.

The amino acid sequence of H245Q is shown in Seq. ID No. 6.

ISOLATION OF PLASMID DNA & TRANSFORMATION: this was carried out by the method of Brinboim & Doly (1979) Nucleic Acids Research 7: 1513.

CELL CULTURE AND EXTRACTION: $E$. $coli$ JM109 transformants were grown to an $OD_{600}$=1.0. Aliquots of cells expressing mutant luciferases from plasmid pPW601a, were subjected to lysis as described in the Promega technical bulletin and the lysed extracts were then stored on ice prior to assay.

ASSAY OF Km OF MUTANT LUCIFERASES: luciferase assays were performed at 21° C. using 100 $\mu$l of assay buffer (20 mM Tricine pH 7.8 containing 2.0 mM $MgSO_4$, 0.1 mM EDTA, 33 mM dithiotheitol, 470 $\mu$M D-luciferin and ATP in the concentration range 6.25–800 μM). Each assay contained 5–10 μl of crude cell extract.

The plots of V against [ATP] and 1/V against 1/[ATP] for mutant H245A are shown in FIG. 2. Such plots kan be used to determine the $K_m$.

The results of each mutation and the recombinant Wild Type are shown in Table 1:

TABLE 1

| Luciferase | $K_m$MgATP (μM) |
|---|---|
| r Wild Type | 66 |
| H245A | 442 |
| H245N | 623 |
| H245Q | 1340 |
| A21SL* | 65 |

*A215L is a thermostable mutant in which amino acid 215 is substituted with lysine (see WO 96/22376 - SECRETARY OF STATE FOR DEFENCE).

ASSAY OF THERMOSTABILITY OF MUTANT LUCIFERASES: the thermostability of H245N & H245Q was also tested, as compared with mutant A215L and the wild-type. Lysed crude extracts of cells containing luciferase activity were incubated at 37° C. for set time periods. The thermostability of the mutant H245A was found to be very similar to that of the recombinant wild-type. The results are shown in Table 2:

TABLE 2

| Enzyme | Remaining activity % | | | |
|---|---|---|---|---|
| | 0 | 2 | 4 | 8 minutes |
| r Wild Type | 100 | 64.8 | 36.6 | 26.6 |
| A215L | 100 | 101 | 88 | 84 |
| H245N | 100 | 96 | 61 | 46 |
| H245Q | 100 | 103 | 78.6 | 51.5 |

PURIFICATION: luciferases, e.g. incorporating the H245Q mutation, may be purified as described in White et al (1996) [supra]. Briefly, the cell lysates are centrifuged at 30000 g for 30 mins and the supernatant is fractionated with ammonium sulphate (30–55%). This fraction is resuspended and desalted. The desalted material was passed through a hydroxyapatite column and eluted with 10–200 mM sodium phosphate containing dithiothreitol. The luciferase containing eluant is dialysed and applied to a Mono Q anion-exchange column. The enzyme can be eluted with 0 to 500 mM NaCl.

EXAMPLE 2

Identification of Corresponding High $K_M$ Mutants

FIG. 3. shows a sequence comparison of one region of P pyralis and the corresponding region of L cruciata as describe din Example 2. In this case it can be seen that amino acid 245 corresponds to 247.

EXAMPLE 3

Expression of Mutant Luciferase in Mammals

This can be achieved by methods analogous to those disclosed by Liu et al (1997) Nature Biotechnology 15: 167–173. In this method cationic liposomes are used to deliver plasmid DNA containing luciferase a gene to mice.

EXAMPLE 4

An in Vivo ATP Assay in Mammals

This can be carried out by methods analogous to those used by Contag et al (1995) Molecular Microbiology 18(4): 593–603. In this method luciferase expression in S typhinurium in mice is monitored using a CCD camera.

EXAMPLE 5

A Kit for an in Vitro ATP Assay

This may be provided as follows: luciferase H245Q; buffer; or dry materials for preparing a buffer; ATP for standards; luciferin; and instructions for carrying out an ATP assay.

EXAMPLE 6

Assay for Determining Cell Behaviour

Figure 4:
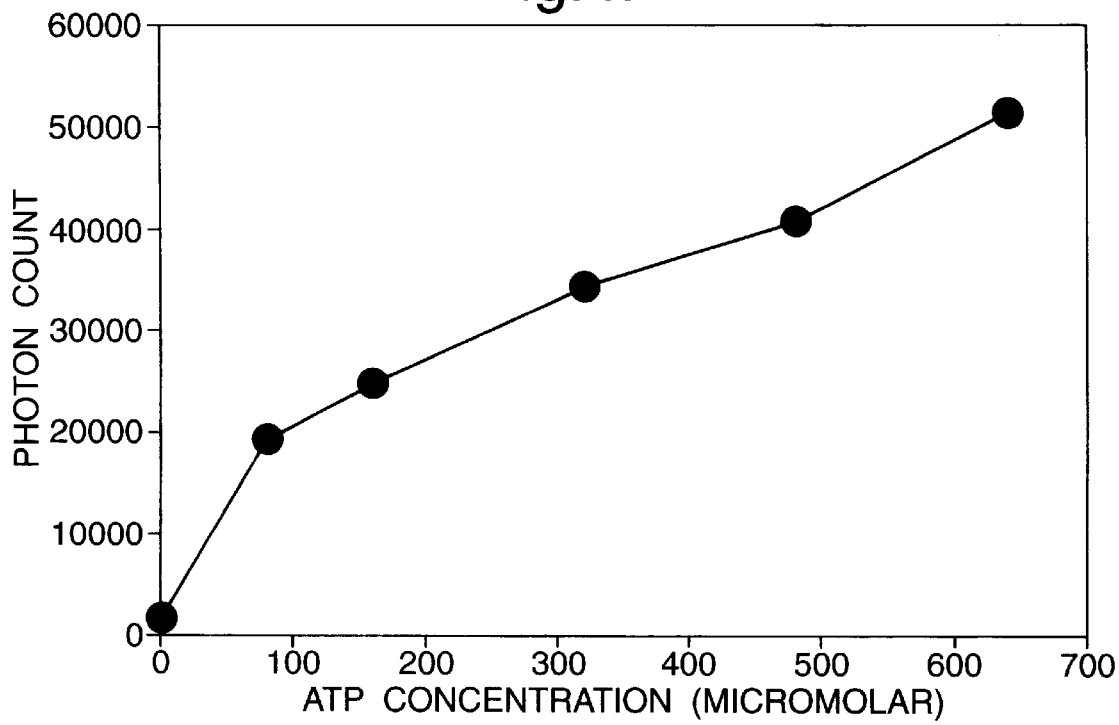

Using a luciferase assay as described in Example 1, a plot of the photon count versus the ATP concentration was prepared for the H245N mutant. The results are shown in FIG. 4.

Figure 5:
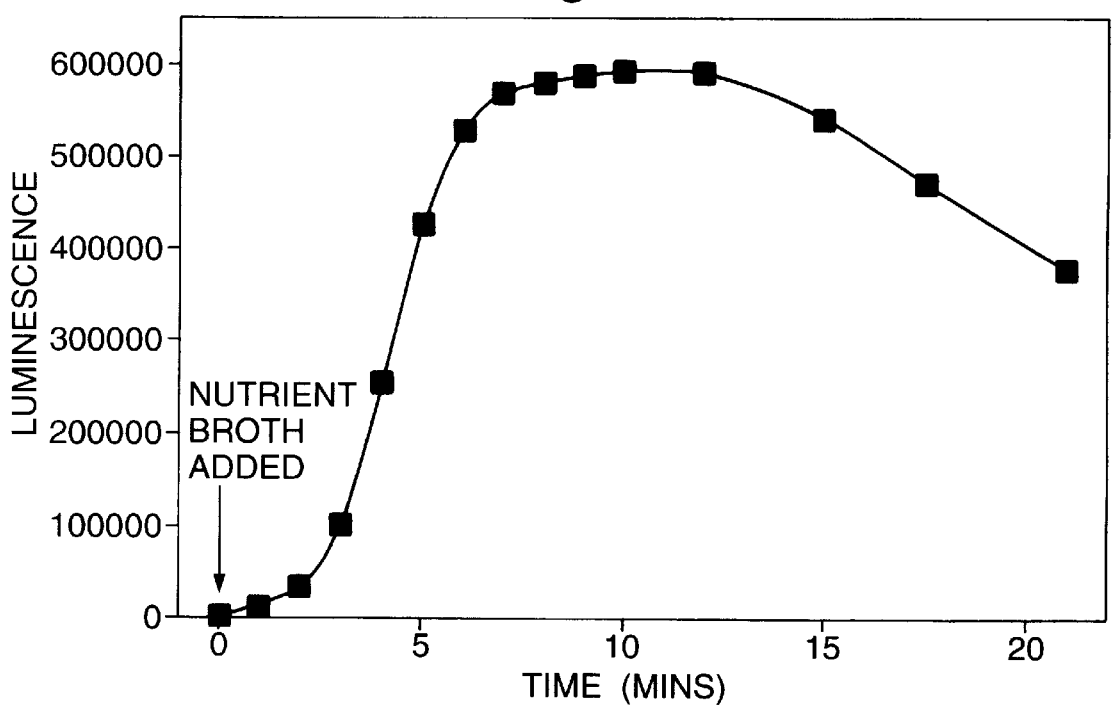

In order to demonstrate how the enzyme of the invention can be used in studying cellular behaviour, a sample of recombinant E.coli cells which expressed the H245N mutant luciferase were rendered dormant by exhaustion of nutrients. The cells were charged with luciferin by 10 minutes immersion in p.H. 5.0 citrate buffer containing 1 mM luciferin. They were then centrifugally washed, resuspended in 1 ml Nutrient Broth and the luminescence monitored. The results are shown in FIG. 5.

Using the mutant luciferase of the invention, the revival and growth of functional cells could be monitored.

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 1722 base pairs
      (B) TYPE: nucleic acid
      (C) STRANDEDNESS: double
      (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Photinus pyralis (ix) FEATURE:
        (A) NAME/KEY: CDS
        (B) LOCATION: 4..1653

(xi) SEQUENCE DESCRIPTION: SEQ ID NO: 1:

| | | | | | |
|---|---|---|---|---|---|
| CAAATGGAAG | ACGCCAAAAA | CATAAAGAAA | GGCCCGGCGC | CATTCTATCC | TCTAGAGGAT | 60 |
| GGAACCGCTG | GAGAGCAACT | GCATAAGGCT | ATGAAGAGAT | ACGCCCTGGT | TCCTGGAACA | 120 |
| ATTGCTTTTA | CAGATGCACA | TATCGAGGTG | AACATCACGT | ACGCGGAATA | CTTCGAAATG | 180 |
| TCCGTTCGGT | TGGCAGAAGC | TATGAAACGA | TATGGGCTGA | ATACAAATCA | CAGAATCGTC | 240 |
| GTATGCAGTG | AAAACTCTCT | TCAATTCTTT | ATGCCGGTGT | TGGGCGCGTT | ATTTATCGGA | 300 |
| GTTGCAGTTG | CGCCCGCGAA | CGACATTTAT | AATGAACGTG | AATTGCTCAA | CAGTATGAAC | 360 |
| ATTTCGCAGC | CTACCGTAGT | GTTTGTTTCC | AAAAAGGGGT | TGCAAAAAAT | TTTGAACGTG | 420 |
| CAAAAAAAT | TACCAATAAT | CCAGAAAATT | ATTATCATGG | ATTCTAAAAC | GGATTACCAG | 480 |
| GGATTTCAGT | CGATGTACAC | GTTCGTCACA | TCTCATCTAC | CTCCCGGTTT | TAATGAATAC | 540 |
| GATTTTGTAC | CAGAGTCCTT | TGATCGTGAC | AAAACAATTG | CACTGATAAT | GAATTCCTCT | 600 |
| GGATCTACTG | GGTTACCTAA | GGGTGTGGCC | CTTCCGCATA | GAACTGCCTG | CGTCAGATTC | 660 |
| TCGCATGCCA | GAGATCCTAT | TTTTGGCAAT | CAAATCATTC | CGGATACTGC | GATTTTAAGT | 720 |
| GTTGTTCCAT | TCCATCACGG | TTTTGGAATG | TTTACTACAC | TCGGATATTT | GATATGTGGA | 780 |
| TTTCGAGTCG | TCTTAATGTA | TAGATTTGAA | GAAGAGCTGT | TTTTACGATC | CCTTCAGGAT | 840 |
| TACAAAATTC | AAAGTGCGTT | GCTAGTACCA | ACCCTATTTT | CATTCTTCGC | CAAAAGCACT | 900 |
| CTGATTGACA | AATACGATTT | ATCTAATTTA | CACGAAATTG | CTTCTGGGGG | CGCACCTCTT | 960 |
| TCGAAAGAAG | TCGGGGAAGC | GGTTGCAAAA | CGCTTCCATC | TTCCAGGGAT | ACGACAAGGA | 1020 |
| TATGGGCTCA | CTGAGACTAC | ATCAGCTATT | CTGATTACAC | CCGAGGGGGA | TGATAAACCG | 1080 |
| GGCGCGGTCG | GTAAAGTTGT | TCCATTTTTT | GAAGCGAAGG | TTGTGGATCT | GGATACCGGG | 1140 |
| AAAACGCTGG | GCGTTAATCA | GAGAGGCGAA | TTATGTGTCA | GAGGACCTAT | GATTATGTCC | 1200 |
| GGTTATGTAA | ACAATCCGGA | AGCGACCAAC | GCCTTGATTG | ACAAGGATGG | ATGGCTACAT | 1260 |
| TCTGGAGACA | TAGCTTACTG | GGACGAAGAC | GAACACTTCT | TCATAGTTGA | CCGCTTGAAG | 1320 |
| TCTTTAATTA | AATACAAAGG | ATATCAGGTG | GCCCCCGCTG | AATTGGAATC | GATATTGTTA | 1380 |
| CAACACCCCA | ACATCTTCGA | CGCGGGCGTG | GCAGGTCTTC | CCGACGATGA | CGCCGGTGAA | 1440 |
| CTTCCCGCCG | CCGTTGTTGT | TTTGGAGCAC | GGAAAGACGA | TGACGGAAAA | AGAGATCGTG | 1500 |
| GATTACGTCG | CCAGTCAAGT | AACAACCGCG | AAAAAGTTGC | GCGGAGGAGT | TGTGTTTGTG | 1560 |
| GACGAAGTAC | CGAAAGGTCT | TACCGGAAAA | CTCGACGCAA | GAAAAATCAG | AGAGATCCTC | 1620 |
| ATAAAGGCCA | AGAAGGGCGG | AAAGTCCAAA | TTGTAAAATG | TAACTGTATT | CAGCGATGAC | 1680 |
| GAAATTCTTA | GCTATTGTAA | TCCTCCGAGG | CCTCGAGGTC | GA | | 1722 |

(2) INFORMATION FOR SEQ ID NO: 2:

(i) SEQUENCE CHARACTERISTICS:
        (A) LENGTH: 35 base pairs
        (B) TYPE: nucleic acid
        (C) STRANDEDNESS: single
        (D) TOPOLOGY: linear

```
       (xi) SEQUENCE DESCRIPTION: SEQ ID NO: 2:

GTTGTTCCAT TCCATGCCGG TTTCGGAATG TTTAC                              35

(2) INFORMATION FOR SEQ ID NO: 3:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (xi) SEQUENCE DESCRIPTION: SEQ ID NO: 3:

GTTGTTCCAT TCCATCAGGG TTTCGGAATG TTTAC                              35

(2) INFORMATION FOR SEQ ID NO: 4:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (xi) SEQUENCE DESCRIPTION: SEQ ID NO: 4:

GTTGTTCCAT TCCATAACGG TTTCGGAATG TTTAC                              35

(2) INFORMATION FOR SEQ ID NO: 5:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (xi) SEQUENCE DESCRIPTION: SEQ ID NO: 5:

GTTGTTCCAT TCCATCACGG TTTTGGAATG TTTAC                              35

(2) INFORMATION FOR SEQ ID NO: 6:

(i) SEQUENCE CHARACTERISTICS:
         (A) LENGTH: 550 amino acids
         (B) TYPE: amino acid
         (C) STRANDEDNESS: single
         (D) TOPOLOGY: unknown (ii) MOLECULE TYPE: protein (iii) HYPOTHETICAL: NO (vi) ORIGINAL SOURCE:
         (A) ORGANISM: Photinus pyralis (ix) FEATURE:
         (A) NAME/KEY: Modified-site
         (B) LOCATION: 245

(xi) SEQUENCE DESCRIPTION: SEQ ID NO: 6:

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80
```

-continued

```
Cys Ser Glu Asn Ser Leu Gln Phe Phe Met Pro Val Leu Gly Ala Leu
                 85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
        115                 120                 125
Ser Lys Lys Gly Leu Gln Lys Ile Leu Asn Val Gln Lys Lys Leu Pro
    130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His Gln Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Ala Gly Glu Leu
465                 470                 475                 480
Pro Ala Ala Val Val Val Leu Glu His Gly Lys Thr Met Thr Glu Lys
                485                 490                 495
```

```
Glu Ile Val Asp Tyr Val Ala Ser Gln Val Thr Thr Ala Lys Lys Leu
                500             505                 510

Arg Gly Gly Val Val Phe Val Asp Glu Val Pro Lys Gly Leu Thr Gly
            515             520                 525

Lys Leu Asp Ala Arg Lys Ile Arg Glu Ile Leu Ile Lys Ala Lys Lys
    530             535                 540

Gly Gly Lys Ser Lys Leu
545             550
```

(2) INFORMATION FOR SEQ ID NO: 7:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO: 7:

```
Ile Ile Pro Asp Thr Ala Ile Leu Ser Val Val Pro Phe His His Gly
1               5                   10                  15

Phe Gly Met Phe Thr Thr Leu Gly Tyr Leu Ile Cys
            20                  25
```

(2) INFORMATION FOR SEQ ID NO: 8:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO: 8:

```
Val Ser Pro Gly Thr Ala Val Leu Thr Val Val Pro Phe His His Gly
1               5                   10                  15

Phe Gly Met Phe Thr Thr Leu Gly Tyr Leu Ile Cys
            20                  25
```

(2) INFORMATION FOR SEQ ID NO: 9:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO: 9:

```
Ile Asp Lys Tyr Asp Leu Ser Asn Leu His Glu Ile Ala Ser Gly Gly
1               5                   10                  15

Ala Pro Leu Ser Lys Glu Val Gly Glu Ala Val Ala Lys Arg Phe His
            20                  25                  30

Leu Pro Gly
        35
```

(2) INFORMATION FOR SEQ ID NO: 10:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO: 10:

```
Leu Asn Lys Tyr Asp Leu Ser Asn Leu Val Glu Ile Ala Ser Gly Gly
1               5                   10                  15

Ala Pro Leu Ser Lys Glu Val Gly Glu Ala Val Ala Arg Arg Phe His
            20                  25                  30
```

Leu Pro Gly
     35

(2) INFORMATION FOR SEQ ID NO: 11:

(i) SEQUENCE CHARACTERISTICS:
        (A) LENGTH: 40 amino acids
        (B) TYPE: amino acid
        (D) TOPOLOGY: linear (xi) SEQUENCE DESCRIPTION: SEQ ID NO: 11:

Arg Phe His Leu Pro Gly Ile Arg Gln Gly Tyr Gly Leu Thr Glu Thr
1               5                  10                  15

Thr Ser Ala Ile Leu Ile Thr Pro Glu Gly Asp Asp Lys Pro Gly Ala
            20                  25                  30

Val Gly Lys Val Val Pro Phe Phe
            35                  40

(2) INFORMATION FOR SEQ ID NO: 12:

(i) SEQUENCE CHARACTERISTICS:
        (A) LENGTH: 40 amino acids
        (B) TYPE: amino acid
        (D) TOPOLOGY: linear (xi) SEQUENCE DESCRIPTION: SEQ ID NO: 12:

Arg Phe Asn Leu Pro Gly Val Arg Gln Gly Tyr Gly Leu Thr Glu Thr
1               5                  10                  15

Thr Ser Ala Ile Ile Ile Thr Pro Glu Gly Asp Asp Lys Pro Gly Ala
            20                  25                  30

Ser Gly Lys Val Val Pro Leu Phe
            35                  40

(2) INFORMATION FOR SEQ ID NO: 13:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1644

(xi) SEQUENCE DESCRIPTION: SEQ ID NO: 13:

ATG GAA AAC ATG GAA AAC GAT GAA AAT ATT GTA GTT GGA CCT AAA CCG      48
Met Glu Asn Met Glu Asn Asp Glu Asn Ile Val Val Gly Pro Lys Pro
1               5                  10                  15

TTT TAC CCT ATC GAA GAG GGA TCT GCT GGA ACA CAA TTA CGC AAA TAC      96
Phe Tyr Pro Ile Glu Glu Gly Ser Ala Gly Thr Gln Leu Arg Lys Tyr
            20                  25                  30

ATG GAG CGA TAT GCA AAA CTT GGC GCA ATT GCT TTT ACA AAT GCA GTT     144
Met Glu Arg Tyr Ala Lys Leu Gly Ala Ile Ala Phe Thr Asn Ala Val
            35                  40                  45

ACT GGT GTT GAT TAT TCT TAC GCC GAA TAC TTG GAG AAA TCA TGT TGT     192
Thr Gly Val Asp Tyr Ser Tyr Ala Glu Tyr Leu Glu Lys Ser Cys Cys
        50                  55                  60

CTA GGA AAA GCT TTG CAA AAT TAT GGT TTG GTT GTT GAT GGA AGA ATT     240
Leu Gly Lys Ala Leu Gln Asn Tyr Gly Leu Val Val Asp Gly Arg Ile
65                  70                  75                  80

GCG TTA TGC AGT GAA AAC TGT GAA GAA TTT TTT ATT CCT GTA ATA GCC     288

```
Ala Leu Cys Ser Glu Asn Cys Glu Glu Phe Phe Ile Pro Val Ile Ala
             85                  90                  95

GGA CTG TTT ATA GGT GTA GGT GTT GCA CCC ACT AAT GAG ATT TAC ACT      336
Gly Leu Phe Ile Gly Val Gly Val Ala Pro Thr Asn Glu Ile Tyr Thr
            100                 105                 110

TTA CGT GAA CTG GTT CAC AGT TTA GGT ATC TCT AAA CCA ACA ATT GTA      384
Leu Arg Glu Leu Val His Ser Leu Gly Ile Ser Lys Pro Thr Ile Val
            115                 120                 125

TTT AGT TCT AAA AAA GGC TTA GAT AAA GTT ATA ACA GTA CAG AAA ACA      432
Phe Ser Ser Lys Lys Gly Leu Asp Lys Val Ile Thr Val Gln Lys Thr
    130                 135                 140

GTA ACT ACT ATT AAA ACC ATT GTT ATA CTA GAT AGC AAA GTT GAT TAT      480
Val Thr Thr Ile Lys Thr Ile Val Ile Leu Asp Ser Lys Val Asp Tyr
145                 150                 155                 160

CGA GGA TAT CAA TGT CTG GAC ACC TTT ATA AAA AGA AAC ACT CCA CCA      528
Arg Gly Tyr Gln Cys Leu Asp Thr Phe Ile Lys Arg Asn Thr Pro Pro
                165                 170                 175

GGT TTT CAA GCA TCC AGT TTC AAA ACT GTG GAA GTT GAC CGT AAA GAA      576
Gly Phe Gln Ala Ser Ser Phe Lys Thr Val Glu Val Asp Arg Lys Glu
            180                 185                 190

CAA GTT GCT CTT ATA ATG AAC TCT TCG GGT TCT ACC GGT TTG CCA AAA      624
Gln Val Ala Leu Ile Met Asn Ser Ser Gly Ser Thr Gly Leu Pro Lys
            195                 200                 205

GGC GTA CAA CTT ACT CAC GAA AAT ACA GTC ACT AGA TTT TCT CAT GCT      672
Gly Val Gln Leu Thr His Glu Asn Thr Val Thr Arg Phe Ser His Ala
            210                 215                 220

AGA GAT CCG ATT TAT GGT AAC CAA GTT TCA CCA GGC ACC GCT GTT TTA      720
Arg Asp Pro Ile Tyr Gly Asn Gln Val Ser Pro Gly Thr Ala Val Leu
225                 230                 235                 240

ACT GTC GTT CCA TTC CAT CAT GGT TTT GGT ATG TTC ACT ACT CTA GGG      768
Thr Val Val Pro Phe His His Gly Phe Gly Met Phe Thr Thr Leu Gly
                245                 250                 255

TAT TTA ATT TGT GGT TTT CGT GTT GTA ATG TTA ACA AAA TTC GAT GAA      816
Tyr Leu Ile Cys Gly Phe Arg Val Val Met Leu Thr Lys Phe Asp Glu
            260                 265                 270

GAA ACA TTT TTA AAA ACT CTA CAA GAT TAT AAA TGT ACA AGT GTT ATT      864
Glu Thr Phe Leu Lys Thr Leu Gln Asp Tyr Lys Cys Thr Ser Val Ile
            275                 280                 285

CTT GTA CCG ACC TTG TTT GCA ATT CTC AAC AAA AGT GAA TTA CTC AAT      912
Leu Val Pro Thr Leu Phe Ala Ile Leu Asn Lys Ser Glu Leu Leu Asn
            290                 295                 300

AAA TAC GAT TTG TCA AAT TTA GTT GAG ATT GCA TCT GGC GGA GCA CCT      960
Lys Tyr Asp Leu Ser Asn Leu Val Glu Ile Ala Ser Gly Gly Ala Pro
305                 310                 315                 320

TTA TCA AAA GAA GTT GGT GAA GCT GTT GCT AGA CGC TTT AAT CTT CCC     1008
Leu Ser Lys Glu Val Gly Glu Ala Val Ala Arg Arg Phe Asn Leu Pro
                325                 330                 335

GGT GTT CGT CAA GGT TAT GGT TTA ACA GAA ACA ACA TCT GCC ATT ATT     1056
Gly Val Arg Gln Gly Tyr Gly Leu Thr Glu Thr Thr Ser Ala Ile Ile
            340                 345                 350

ATT ACA CCA GAA GGA GAC GAT AAA CCA GGA GCT TCT GGA AAA GTC GTG     1104
Ile Thr Pro Glu Gly Asp Asp Lys Pro Gly Ala Ser Gly Lys Val Val
            355                 360                 365

CCG TTG TTT AAA GCA AAA GTT ATT GAT CTT GAT ACC AAA AAA TCT TTA     1152
Pro Leu Phe Lys Ala Lys Val Ile Asp Leu Asp Thr Lys Lys Ser Leu
            370                 375                 380

GGT CCT AAC AGA CGT GGA GAA GTT TGT GTT AAA GGA CCT ATG CTT ATG     1200
Gly Pro Asn Arg Arg Gly Glu Val Cys Val Lys Gly Pro Met Leu Met
385                 390                 395                 400
```

```
AAA GGT TAT GTA AAT AAT CCA GAA GCA ACA AAA GAA CTT ATT GAC GAA      1248
Lys Gly Tyr Val Asn Asn Pro Glu Ala Thr Lys Glu Leu Ile Asp Glu
            405                 410                 415

GAA GGT TGG CTG CAC ACC GGA GAT ATT GGA TAT TAT GAT GAA GAA AAA      1296
Glu Gly Trp Leu His Thr Gly Asp Ile Gly Tyr Tyr Asp Glu Glu Lys
            420                 425                 430

CAT TTC TTT ATT GTC GAT CGT TTG AAG TCT TTA ATC AAA TAC AAA GGA      1344
His Phe Phe Ile Val Asp Arg Leu Lys Ser Leu Ile Lys Tyr Lys Gly
            435                 440                 445

TAC CAA GTA CCA CCT GCC GAA TTA GAA TCC GTT CTT TTG CAA CAT CCA      1392
Tyr Gln Val Pro Pro Ala Glu Leu Glu Ser Val Leu Leu Gln His Pro
        450                 455                 460

TCT ATC TTT GAT GCT GGT GTT GCC GGC GTT CCT GAT CCT GTA GCT GGC      1440
Ser Ile Phe Asp Ala Gly Val Ala Gly Val Pro Asp Pro Val Ala Gly
465                 470                 475                 480

GAG CTT CCA GGA GCC GTT GTT GTA CTG GAA AGC GGA AAA AAT ATG ACC      1488
Glu Leu Pro Gly Ala Val Val Val Leu Glu Ser Gly Lys Asn Met Thr
            485                 490                 495

GAA AAA GAA GTA ATG GAT TAT GTT GCA AGT CAA GTT TCA AAT GCA AAA      1536
Glu Lys Glu Val Met Asp Tyr Val Ala Ser Gln Val Ser Asn Ala Lys
            500                 505                 510

CGT TTA CGT GGT GGT GTT CGT TTT GTG GAT GAA GTA CCT AAA GGT CTT      1584
Arg Leu Arg Gly Gly Val Arg Phe Val Asp Glu Val Pro Lys Gly Leu
            515                 520                 525

ACT GGA AAA ATT GAC GGC AGA GCA ATT AGA GAA ATC CTT AAG AAA CCA      1632
Thr Gly Lys Ile Asp Gly Arg Ala Ile Arg Glu Ile Leu Lys Lys Pro
530                 535                 540

GTT GCT AAG ATG                                                      1644
Val Ala Lys Met
545

(2) INFORMATION FOR SEQ ID NO: 14:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO: 14:

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
                20                  25                  30

Met Glu Arg Tyr Ala Lys Leu Gly Ala Ile Ala Phe Thr Asn Ala Val
            35                  40                  45

Thr Gly Val Asp Tyr Ser Tyr Ala Glu Tyr Leu Glu Lys Ser Cys Cys
        50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
        130                 135                 140
```

```
Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
                180                 185                 190

Gln Val Ala Leu Ile Met Asn Ser Ser Gly Ser Thr Gly Leu Pro Lys
                195                 200                 205

Gly Val Gln Leu Thr His Glu Asn Thr Val Thr Arg Phe Ser His Ala
210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
                260                 265                 270

Glu Thr Phe Leu Lys Thr Leu Gln Asp Tyr Lys Cys Thr Ser Val Ile
                275                 280                 285

Leu Val Pro Thr Leu Phe Ala Ile Leu Asn Lys Ser Glu Leu Leu Asn
290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
                340                 345                 350

Ile Thr Pro Glu Gly Asp Asp Lys Pro Gly Ala Ser Gly Lys Val Val
                355                 360                 365

Pro Leu Phe Lys Ala Lys Val Ile Asp Leu Asp Thr Lys Lys Ser Leu
                370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
                405                 410                 415

Glu Gly Trp Leu His Thr Gly Asp Ile Gly Tyr Tyr Asp Glu Glu Lys
                420                 425                 430

His Phe Phe Ile Val Asp Arg Leu Lys Ser Leu Ile Lys Tyr Lys Gly
                435                 440                 445

Tyr Gln Val Pro Pro Ala Glu Leu Glu Ser Val Leu Leu Gln His Pro
450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
                485                 490                 495

Glu Lys Glu Val Met Asp Tyr Val Ala Ser Gln Val Ser Asn Ala Lys
                500                 505                 510

Arg Leu Arg Gly Gly Val Arg Phe Val Asp Glu Val Pro Lys Gly Leu
                515                 520                 525

Thr Gly Lys Ile Asp Gly Arg Ala Ile Arg Glu Ile Leu Lys Lys Pro
                530                 535                 540

Val Ala Lys Met
545
```

(2) INFORMATION FOR SEQ ID NO: 15:

(i) SEQUENCE CHARACTERISTICS:
        (A) LENGTH: 1644 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..1644

(xi) SEQUENCE DESCRIPTION: SEQ ID NO: 15:

```
ATG AAC ATG GAG AAC GAT GAA AAT ATT GTG TAT GGT CCT GAA CCA        48
Met Glu Asn Met Glu Asn Asp Glu Asn Ile Val Tyr Gly Pro Glu Pro
 1               5                  10                  15

TTT TAC CCT ATT GAA GAG GGA TCT GCT GGA GCA CAA TTG CGC AAG TAT    96
Phe Tyr Pro Ile Glu Glu Gly Ser Ala Gly Ala Gln Leu Arg Lys Tyr
             20                  25                  30

ATG GAT CGA TAT GCA AAA CTT GGA GCA ATT GCT TTT ACT AAC GCA CTT   144
Met Asp Arg Tyr Ala Lys Leu Gly Ala Ile Ala Phe Thr Asn Ala Leu
         35                  40                  45

ACC GGT GTC GAT TAT ACG TAC GCC GAA TAC TTA GAA AAA TCA TGC TGT   192
Thr Gly Val Asp Tyr Thr Tyr Ala Glu Tyr Leu Glu Lys Ser Cys Cys
 50                  55                  60

CTA GGA GAG GCT TTA AAG AAT TAT GGT TTG GTT GTT GAT GGA AGA ATT   240
Leu Gly Glu Ala Leu Lys Asn Tyr Gly Leu Val Val Asp Gly Arg Ile
 65                  70                  75                  80

GCG TTA TGC AGT GAA AAC TGT GAA GAA TTC TTT ATT CCT GTA TTA GCC   288
Ala Leu Cys Ser Glu Asn Cys Glu Glu Phe Phe Ile Pro Val Leu Ala
                 85                  90                  95

GGT TTA TTT ATA GGT GTC GGT GTG GCT CCA ACT AAT GAG ATT TAC ACT   336
Gly Leu Phe Ile Gly Val Gly Val Ala Pro Thr Asn Glu Ile Tyr Thr
            100                 105                 110

CTA CGT GAA TTG GTT CAC AGT TTA GGC ATC TCT AAG CCA ACA ATT GTA   384
Leu Arg Glu Leu Val His Ser Leu Gly Ile Ser Lys Pro Thr Ile Val
        115                 120                 125

TTT AGT TCT AAA AAA GGA TTA GAT AAA GTT ATA ACT GTA CAA AAA ACG   432
Phe Ser Ser Lys Lys Gly Leu Asp Lys Val Ile Thr Val Gln Lys Thr
    130                 135                 140

GTA ACT GCT ATT AAA ACC ATT GTT ATA TTG GAC AGC AAA GTG GAT TAT   480
Val Thr Ala Ile Lys Thr Ile Val Ile Leu Asp Ser Lys Val Asp Tyr
145                 150                 155                 160

AGA GGT TAT CAA TCC ATG GAC AAC TTT ATT AAA AAA AAC ACT CCA CAA   528
Arg Gly Tyr Gln Ser Met Asp Asn Phe Ile Lys Lys Asn Thr Pro Gln
                165                 170                 175

GGT TTC AAA GGA TCA AGT TTT AAA ACT GTA GAA GTT AAC CGC AAA GAA   576
Gly Phe Lys Gly Ser Ser Phe Lys Thr Val Glu Val Asn Arg Lys Glu
            180                 185                 190

CAA GTT GCT CTT ATA ATG AAC TCT TCG GGT TCA ACC GGT TTG CCA AAA   624
Gln Val Ala Leu Ile Met Asn Ser Ser Gly Ser Thr Gly Leu Pro Lys
        195                 200                 205

GGT GTG CAA CTT ACT CAT GAA AAT GCA GTC ACT AGA TTT TCT CAC GCT   672
Gly Val Gln Leu Thr His Glu Asn Ala Val Thr Arg Phe Ser His Ala
    210                 215                 220

AGA GAT CCA ATT TAT GGA AAC CAA GTT TCA CCA GGC ACG GCT ATT TTA   720
Arg Asp Pro Ile Tyr Gly Asn Gln Val Ser Pro Gly Thr Ala Ile Leu
225                 230                 235                 240

ACT GTA GTA CCA TTC CAT CAT GGT TTT GGT ATG TTT ACT ACT TTA GGC   768
Thr Val Val Pro Phe His His Gly Phe Gly Met Phe Thr Thr Leu Gly
                245                 250                 255
```

```
TAT CTA ACT TGT GGT TTT CGT ATT GTC ATG TTA ACG AAA TTT GAC GAA    816
Tyr Leu Thr Cys Gly Phe Arg Ile Val Met Leu Thr Lys Phe Asp Glu
            260                 265                 270

GAG ACT TTT TTA AAA ACA CTG CAA GAT TAC AAA TGT TCA AGC GTT ATT    864
Glu Thr Phe Leu Lys Thr Leu Gln Asp Tyr Lys Cys Ser Ser Val Ile
            275                 280                 285

CTT GTA CCG ACT TTG TTT GCA ATT CTT AAT AGA AGT GAA TTA CTC GAT    912
Leu Val Pro Thr Leu Phe Ala Ile Leu Asn Arg Ser Glu Leu Leu Asp
    290                 295                 300

AAA TAT GAT TTA TCA AAT TTA GTT GAA ATT GCA TCT GGC GGA GCA CCT    960
Lys Tyr Asp Leu Ser Asn Leu Val Glu Ile Ala Ser Gly Gly Ala Pro
305                 310                 315                 320

TTA TCT AAA GAA ATT GGT GAA GCT GTT GCT AGA CGT TTT AAT TTA CCG   1008
Leu Ser Lys Glu Ile Gly Glu Ala Val Ala Arg Arg Phe Asn Leu Pro
                325                 330                 335

GGT GTT CGT CAA GGC TAT GGT TTA ACA GAA ACA ACC TCT GCA ATT ATT   1056
Gly Val Arg Gln Gly Tyr Gly Leu Thr Glu Thr Thr Ser Ala Ile Ile
            340                 345                 350

ATC ACA CCG GAA GGC GAT GAT AAA CCA GGT GCT TCT GGC AAA GTT GTG   1104
Ile Thr Pro Glu Gly Asp Asp Lys Pro Gly Ala Ser Gly Lys Val Val
            355                 360                 365

CCA TTA TTT AAA GCA AAA GTT ATC GAT CTT GAT ACT AAA AAA ACT TTG   1152
Pro Leu Phe Lys Ala Lys Val Ile Asp Leu Asp Thr Lys Lys Thr Leu
    370                 375                 380

GGC CCG AAC AGA CGT GGA GAA GTT TGT GTA AAG GGT CCT ATG CTT ATG   1200
Gly Pro Asn Arg Arg Gly Glu Val Cys Val Lys Gly Pro Met Leu Met
385                 390                 395                 400

AAA GGT TAT GTA GAT AAT CCA GAA GCA ACA AGA GAA ATC ATA GAT GAA   1248
Lys Gly Tyr Val Asp Asn Pro Glu Ala Thr Arg Glu Ile Ile Asp Glu
                405                 410                 415

GAA GGT TGG TTG CAC ACA GGA GAT ATT GGG TAT TAC GAT GAA GAA AAA   1296
Glu Gly Trp Leu His Thr Gly Asp Ile Gly Tyr Tyr Asp Glu Glu Lys
            420                 425                 430

CAT TTC TTT ATC GTG GAT CGT TTG AAG TCT TTA ATC AAA TAC AAA GGA   1344
His Phe Phe Ile Val Asp Arg Leu Lys Ser Leu Ile Lys Tyr Lys Gly
            435                 440                 445

TAT CAA GTA CCA CCT GCT GAA TTA GAA TCT GTT CTT TTG CAA CAT CCA   1392
Tyr Gln Val Pro Pro Ala Glu Leu Glu Ser Val Leu Leu Gln His Pro
    450                 455                 460

AAT ATT TTT GAT GCC GGC GTT GCT GGC GTT CCA GAT CCT ATA GCT GGT   1440
Asn Ile Phe Asp Ala Gly Val Ala Gly Val Pro Asp Pro Ile Ala Gly
465                 470                 475                 480

GAG CTT CCG GGA GCT GTT GTT GTA CTT GAA AAA GGA AAA TCT ATG ACT   1488
Glu Leu Pro Gly Ala Val Val Val Leu Glu Lys Gly Lys Ser Met Thr
                485                 490                 495

GAA AAA GAA GTA ATG GAT TAC GTT GCT AGT CAA GTT TCA AAT GCA AAA   1536
Glu Lys Glu Val Met Asp Tyr Val Ala Ser Gln Val Ser Asn Ala Lys
            500                 505                 510

CGT TTG CGT GGT GGT GTC CGT TTT GTG GAC GAA GTA CCT AAA GGT CTC   1584
Arg Leu Arg Gly Gly Val Arg Phe Val Asp Glu Val Pro Lys Gly Leu
            515                 520                 525

ACT GGT AAA ATT GAC GGT AAA GCA ATT AGA GAA ATA CTG AAG AAA CCA   1632
Thr Gly Lys Ile Asp Gly Lys Ala Ile Arg Glu Ile Leu Lys Lys Pro
    530                 535                 540

GTT GCT AAG ATG                                                   1644
Val Ala Lys Met
545
```

(2) INFORMATION FOR SEQ ID NO: 16:

(i) SEQUENCE CHARACTERISTICS:
    (A) LENGTH: 548 amino acids
    (B) TYPE: amino acid
    (D) TOPOLOGY: linear (ii) MOLECULE TYPE: protein (xi) SEQUENCE DESCRIPTION: SEQ ID NO: 16:

```
Met Glu Asn Met Glu Asn Asp Glu Asn Ile Val Tyr Gly Pro Glu Pro
 1               5                  10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ala Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Val Ile
        275                 280                 285

Leu Val Pro Thr Leu Phe Ala Ile Leu Asn Arg Ser Glu Leu Leu Asp
    290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365
```

-continued

```
Pro Leu Phe Lys Ala Lys Val Ile Asp Leu Asp Thr Lys Lys Thr Leu
    370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
                420                 425                 430

His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Ile Ala Gly
465                 470                 475                 480

Glu Leu Pro Gly Ala Val Val Leu Glu Lys Gly Lys Ser Met Thr
                485                 490                 495

Glu Lys Glu Val Met Asp Tyr Val Ala Ser Gln Val Ser Asn Ala Lys
                500                 505                 510

Arg Leu Arg Gly Gly Val Arg Phe Val Asp Glu Val Pro Lys Gly Leu
            515                 520                 525

Thr Gly Lys Ile Asp Gly Lys Ala Ile Arg Glu Ile Leu Lys Lys Pro
    530                 535                 540

Val Ala Lys Met
545
```

(2) INFORMATION FOR SEQ ID NO: 17:

(i) SEQUENCE CHARACTERISTICS:
        (A) LENGTH: 2009 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 69..1715

(xi) SEQUENCE DESCRIPTION: SEQ ID NO: 17:

```
GGAATTCGGC ACGAGGTTAC AATTACAACT TCGAAGTCCC TAAACGGTAG AGGAAAAGTT      60

TTTGAAAA ATG GAA ATG GAA AAG GAG GAG AAT GTT GTA TAT GGC CCT CTG     110
         Met Glu Met Glu Lys Glu Glu Asn Val Val Tyr Gly Pro Leu
           1               5                  10

CCA TTC TAC CCC ATT GAA GAA GGA TCA GCT GGA ATT CAG TTG CAT AAG     158
Pro Phe Tyr Pro Ile Glu Glu Gly Ser Ala Gly Ile Gln Leu His Lys
 15                  20                  25                  30

TAC ATG CAT CAA TAT GCC AAA CTT GGA GCA ATT GCT TTT AGT AAC GCC     206
Tyr Met His Gln Tyr Ala Lys Leu Gly Ala Ile Ala Phe Ser Asn Ala
            35                  40                  45

CTT ACT GGA GTT GAC ATT TCT TAC CAA GAA TAC TTT GAT ATT ACA TGT     254
Leu Thr Gly Val Asp Ile Ser Tyr Gln Glu Tyr Phe Asp Ile Thr Cys
         50                  55                  60

CGT TTA GCT GAG GCC ATG AAA AAC TTT GGT ATG AAA CCG GAA GAA CAT     302
Arg Leu Ala Glu Ala Met Lys Asn Phe Gly Met Lys Pro Glu Glu His
     65                  70                  75

ATT GCT TTG TGC AGT GAA AAT TGT GAA GAA TTT TTC ATC CCT GTA CTT     350
Ile Ala Leu Cys Ser Glu Asn Cys Glu Glu Phe Phe Ile Pro Val Leu
 80                  85                  90
```

```
GCT GGT CTT TAC ATT GGG GTA GCT GTT GCA CCT ACT AAT GAA ATT TAC         398
Ala Gly Leu Tyr Ile Gly Val Ala Val Ala Pro Thr Asn Glu Ile Tyr
 95             100                 105                 110

ACA TTG CGT GAA CTT AAT CAT AGT TTG GGC ATC GCA CAA CCA ACT ATT         446
Thr Leu Arg Glu Leu Asn His Ser Leu Gly Ile Ala Gln Pro Thr Ile
             115                 120                 125

GTA TTC AGC TCC AGA AAA GGC TTA CCT AAA GTT TTA GAA GTG CAA AAA         494
Val Phe Ser Ser Arg Lys Gly Leu Pro Lys Val Leu Glu Val Gln Lys
         130                 135                 140

ACA GTT ACA TGC ATC AAA AAA ATT GTT ATT TTA GAT AGT AAA GTA AAC         542
Thr Val Thr Cys Ile Lys Lys Ile Val Ile Leu Asp Ser Lys Val Asn
                 145                 150                 155

TTT GGG GGC CAC GAT TGT ATG GAA ACT TTT ATT AAG AAA CAT GTA GAA         590
Phe Gly Gly His Asp Cys Met Glu Thr Phe Ile Lys Lys His Val Glu
    160                 165                 170

TTA GGT TTT CAA CCA AGT AGC TTT GTA CCC ATT GAT GTA AAG AAC CGT         638
Leu Gly Phe Gln Pro Ser Ser Phe Val Pro Ile Asp Val Lys Asn Arg
175             180                 185                 190

AAA CAA CAC GTT GCT TTG CTT ATG AAT TCT TCT GGC TCT ACT GGT TTA         686
Lys Gln His Val Ala Leu Leu Met Asn Ser Ser Gly Ser Thr Gly Leu
                 195                 200                 205

CCT AAA GGT GTA CGA ATT ACC CAC GAA GGT GCA GTT ACA AGA TTC TCA         734
Pro Lys Gly Val Arg Ile Thr His Glu Gly Ala Val Thr Arg Phe Ser
        210                 215                 220

CAC GCT AAG GAT CCA ATT TAC GGA AAC CAA GTT TCA CCT GGT ACT GCT         782
His Ala Lys Asp Pro Ile Tyr Gly Asn Gln Val Ser Pro Gly Thr Ala
            225                 230                 235

ATT TTA ACT GTC GTT CCG TTC CAT CAT GGA TTT GGA ATG TTT ACC ACT         830
Ile Leu Thr Val Val Pro Phe His His Gly Phe Gly Met Phe Thr Thr
    240                 245                 250

TTA GGA TAC TTT GCT TGT GGA TAC CGT GTT GTA ATG TTA ACA AAA TTT         878
Leu Gly Tyr Phe Ala Cys Gly Tyr Arg Val Val Met Leu Thr Lys Phe
255             260                 265                 270

GAT GAA GAA CTA TTT TTG AGA ACT TTG CAA GAT TAT AAG TGT ACC AGT         926
Asp Glu Glu Leu Phe Leu Arg Thr Leu Gln Asp Tyr Lys Cys Thr Ser
                275                 280                 285

GTT ATT CTG GTA CCA ACG TTA TTT GCT ATT CTC AAC AAG AGT GAA TTG         974
Val Ile Leu Val Pro Thr Leu Phe Ala Ile Leu Asn Lys Ser Glu Leu
        290                 295                 300

ATC GAT AAG TTC GAT TTA TCT AAT CTA ACT GAA ATT GCT TCT GGT GGA        1022
Ile Asp Lys Phe Asp Leu Ser Asn Leu Thr Glu Ile Ala Ser Gly Gly
            305                 310                 315

GCT CCT TTG GCA AAA GAA GTT GGC GAA GCA GTC GCT AGA AGA TTT AAT        1070
Ala Pro Leu Ala Lys Glu Val Gly Glu Ala Val Ala Arg Arg Phe Asn
    320                 325                 330

CTA CCC GGT GTC CGT CAG GGT TAC GGA TTA ACA GAA ACG ACA TCT GCA        1118
Leu Pro Gly Val Arg Gln Gly Tyr Gly Leu Thr Glu Thr Thr Ser Ala
335             340                 345                 350

TTT ATT ATT ACC CCA GAA GGT GAT GAT AAA CCT GGA GCA TCT GGA AAA        1166
Phe Ile Ile Thr Pro Glu Gly Asp Asp Lys Pro Gly Ala Ser Gly Lys
                355                 360                 365

GTA GTA CCC TTA TTC AAA GTA AAA GTT ATT GAT CTT GAC ACT AAA AAA        1214
Val Val Pro Leu Phe Lys Val Lys Val Ile Asp Leu Asp Thr Lys Lys
        370                 375                 380

ACT TTG GGT GTC AAC CGA CGA GGA GAG ATC TGT GTA AAA GGA CCC AGT        1262
Thr Leu Gly Val Asn Arg Arg Gly Glu Ile Cys Val Lys Gly Pro Ser
            385                 390                 395

CTT ATG TTA GGC TAC TCG AAC AAT CCG GAA GCA ACA AGA GAA ACT ATT        1310
Leu Met Leu Gly Tyr Ser Asn Asn Pro Glu Ala Thr Arg Glu Thr Ile
    400                 405                 410
```

-continued

```
GAT GAA GAG GGT TGG TTG CAC ACA GGA GAT ATT GGA TAT TAC GAC GAA    1358
Asp Glu Glu Gly Trp Leu His Thr Gly Asp Ile Gly Tyr Tyr Asp Glu
415                 420                 425                 430

GAC GAA CAT TTC TTC ATT GTC GAT CGT TTG AAA TCA TTA ATC AAA TAC    1406
Asp Glu His Phe Phe Ile Val Asp Arg Leu Lys Ser Leu Ile Lys Tyr
                435                 440                 445

AAG GGG TAC CAG GTA CCA CCT GCT GAA TTG GAA TCC GTT CTT TTG CAA    1454
Lys Gly Tyr Gln Val Pro Pro Ala Glu Leu Glu Ser Val Leu Leu Gln
            450                 455                 460

CAT CCA AAT ATA TTT GAT GCT GGT GTG GCT GGT GTC CCC GAT CCC GAT    1502
His Pro Asn Ile Phe Asp Ala Gly Val Ala Gly Val Pro Asp Pro Asp
                465                 470                 475

GCT GGC GAA CTT CCA GGG GCT GTA GTT GTA ATG GAA AAA GGA AAA ACT    1550
Ala Gly Glu Leu Pro Gly Ala Val Val Val Met Glu Lys Gly Lys Thr
480                 485                 490

ATG ACT GAA AAG GAA ATT GTG GAT TAT GTT AAT AGT CAA GTA GTG AAC    1598
Met Thr Glu Lys Glu Ile Val Asp Tyr Val Asn Ser Gln Val Val Asn
495                 500                 505                 510

CAC AAA CGT CTG CGT GGT GGC GTT CGT TTT GTG GAT GAA GTA CCT AAA    1646
His Lys Arg Leu Arg Gly Gly Val Arg Phe Val Asp Glu Val Pro Lys
                515                 520                 525

GGT CTA ACT GGT AAA ATT GAT GCT AAA GTA ATT AGA GAA ATT CTT AAG    1694
Gly Leu Thr Gly Lys Ile Asp Ala Lys Val Ile Arg Glu Ile Leu Lys
            530                 535                 540

AAA CCA CAA GCC AAG ATG TAAATCAGTC AAAATGCTAT TCATGTAACT           1742
Lys Pro Gln Ala Lys Met
                545

AAACTACTCA TAAGAAGACA ATTTAAAATT AAGTCATTAC ACACTTAGTG TTATATCTCA  1802

AAAGTAGTGG GAGTTTGACA TTTATCTCAA TAATTTATCG AATGGATGCT TGTATTAGTT  1862

TCTTATTGTT AATTATAGCT TTAAAGAACG ACTCCTTTAA TATATATTTA CTTGCATTCC  1922

AATGGTTATA TTGTAACGGG CACGTTTCCC TGATATGTGT GAAATATACG TCAATTGCAT  1982

TATTAAAAAA AAAAAAAAAA AAAAAAA                                     2009
```

(2) INFORMATION FOR SEQ ID NO: 18:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO: 18:

```
Met Glu Met Glu Lys Glu Glu Asn Val Val Tyr Gly Pro Leu Pro Phe
1               5                   10                  15

Tyr Pro Ile Glu Glu Gly Ser Ala Gly Ile Gln Leu His Lys Tyr Met
                20                  25                  30

His Gln Tyr Ala Lys Leu Gly Ala Ile Ala Phe Ser Asn Ala Leu Thr
            35                  40                  45

Gly Val Asp Ile Ser Tyr Gln Glu Tyr Phe Asp Ile Thr Cys Arg Leu
        50                  55                  60

Ala Glu Ala Met Lys Asn Phe Gly Met Lys Pro Glu Glu His Ile Ala
65                  70                  75                  80

Leu Cys Ser Glu Asn Cys Glu Glu Phe Phe Ile Pro Val Leu Ala Gly
                85                  90                  95

Leu Tyr Ile Gly Val Ala Val Ala Pro Thr Asn Glu Ile Tyr Thr Leu
                100                 105                 110
```

-continued

```
Arg Glu Leu Asn His Ser Leu Gly Ile Ala Gln Pro Thr Ile Val Phe
            115                 120                 125
Ser Ser Arg Lys Gly Leu Pro Lys Val Leu Glu Val Gln Lys Thr Val
        130                 135                 140
Thr Cys Ile Lys Lys Ile Val Ile Leu Asp Ser Lys Val Asn Phe Gly
145                 150                 155                 160
Gly His Asp Cys Met Glu Thr Phe Ile Lys Lys His Val Glu Leu Gly
                165                 170                 175
Phe Gln Pro Ser Ser Phe Val Pro Ile Asp Val Lys Asn Arg Lys Gln
            180                 185                 190
His Val Ala Leu Leu Met Asn Ser Ser Gly Ser Thr Gly Leu Pro Lys
        195                 200                 205
Gly Val Arg Ile Thr His Glu Gly Ala Val Thr Arg Phe Ser His Ala
    210                 215                 220
Lys Asp Pro Ile Tyr Gly Asn Gln Val Ser Pro Gly Thr Ala Ile Leu
225                 230                 235                 240
Thr Val Val Pro Phe His His Gly Phe Gly Met Phe Thr Thr Leu Gly
                245                 250                 255
Tyr Phe Ala Cys Gly Tyr Arg Val Val Met Leu Thr Lys Phe Asp Glu
            260                 265                 270
Glu Leu Phe Leu Arg Thr Leu Gln Asp Tyr Lys Cys Thr Ser Val Ile
        275                 280                 285
Leu Val Pro Thr Leu Phe Ala Ile Leu Asn Lys Ser Glu Leu Ile Asp
        290                 295                 300
Lys Phe Asp Leu Ser Asn Leu Thr Glu Ile Ala Ser Gly Gly Ala Pro
305                 310                 315                 320
Leu Ala Lys Glu Val Gly Glu Ala Val Ala Arg Arg Phe Asn Leu Pro
                325                 330                 335
Gly Val Arg Gln Gly Tyr Gly Leu Thr Glu Thr Thr Ser Ala Phe Ile
            340                 345                 350
Ile Thr Pro Glu Gly Asp Asp Lys Pro Gly Ala Ser Gly Lys Val Val
        355                 360                 365
Pro Leu Phe Lys Val Lys Val Ile Asp Leu Asp Thr Lys Lys Thr Leu
    370                 375                 380
Gly Val Asn Arg Arg Gly Glu Ile Cys Val Lys Gly Pro Ser Leu Met
385                 390                 395                 400
Leu Gly Tyr Ser Asn Asn Pro Glu Ala Thr Arg Glu Thr Ile Asp Glu
                405                 410                 415
Glu Gly Trp Leu His Thr Gly Asp Ile Gly Tyr Tyr Asp Glu Asp Glu
            420                 425                 430
His Phe Phe Ile Val Asp Arg Leu Lys Ser Leu Ile Lys Tyr Lys Gly
        435                 440                 445
Tyr Gln Val Pro Pro Ala Glu Leu Glu Ser Val Leu Leu Gln His Pro
    450                 455                 460
Asn Ile Phe Asp Ala Gly Val Ala Gly Val Pro Asp Pro Asp Ala Gly
465                 470                 475                 480
Glu Leu Pro Gly Ala Val Val Met Glu Lys Gly Lys Thr Met Thr
                485                 490                 495
Glu Lys Glu Ile Val Asp Tyr Val Asn Ser Gln Val Asn His Lys
            500                 505                 510
Arg Leu Arg Gly Gly Val Arg Phe Val Asp Glu Val Pro Lys Gly Leu
        515                 520                 525
```

```
Thr Gly Lys Ile Asp Ala Lys Val Ile Arg Glu Ile Leu Lys Lys Pro
    530             535                 540

Gln Ala Lys Met
545

(2) INFORMATION FOR SEQ ID NO: 19:

(i) SEQUENCE CHARACTERISTICS:
        (A) LENGTH: 1725 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 32..1675

(xi) SEQUENCE DESCRIPTION: SEQ ID NO: 19:

GAGACACTAA CGCGCTAATA TCATTGCAAG A ATG GAA GAT GCA AAA AAT ATT         52
                                  Met Glu Asp Ala Lys Asn Ile
                                   1               5

ATG CAC GGT CCA GCG CCA TTC TAT CCT TTG GAG GAT GGA ACT GCT GGA       100
Met His Gly Pro Ala Pro Phe Tyr Pro Leu Glu Asp Gly Thr Ala Gly
            10                  15                  20

GAA CAA TTG CAC AAA GCA ATG AAG AGG TAT GCA CAG GTT CCA GGG ACA       148
Glu Gln Leu His Lys Ala Met Lys Arg Tyr Ala Gln Val Pro Gly Thr
 25                  30                  35

ATT GCT TTT ACT GAT GCG CAT GCA GAG GTA AAT ATT ACA TAT TCC GAA       196
Ile Ala Phe Thr Asp Ala His Ala Glu Val Asn Ile Thr Tyr Ser Glu
 40                  45                  50                  55

TAT TTT GAA ATG GCT TGC CGG TTA GCC GAA ACT ATG AAG AGG TAC GGA       244
Tyr Phe Glu Met Ala Cys Arg Leu Ala Glu Thr Met Lys Arg Tyr Gly
                 60                  65                  70

CTT GGT TTA CAA CAC CAC ATT GCT GTT TGT AGC GAA AAT TCT CTT CAG       292
Leu Gly Leu Gln His His Ile Ala Val Cys Ser Glu Asn Ser Leu Gln
             75                  80                  85

TTT TTT ATG CCT GTA TGC GGG GCT CTA TTT ATT GGA GTT GGA GTT GCA       340
Phe Phe Met Pro Val Cys Gly Ala Leu Phe Ile Gly Val Gly Val Ala
         90                  95                 100

TCA ACA AAT GAT ATT TAC AAT GAA CGT GAA TTA TAC AAC AGT TTG TCC       388
Ser Thr Asn Asp Ile Tyr Asn Glu Arg Glu Leu Tyr Asn Ser Leu Ser
    105                 110                 115

ATA TCA CAA CCT ACA ATA GTA TCC TGT TCC AAA AGA GCG CTG CAA AAA       436
Ile Ser Gln Pro Thr Ile Val Ser Cys Ser Lys Arg Ala Leu Gln Lys
120                 125                 130                 135

ATC CTA GGG GTA CAA AAG AAA TTA CCT ATA ATT CAG AAA ATT GTT ATT       484
Ile Leu Gly Val Gln Lys Lys Leu Pro Ile Ile Gln Lys Ile Val Ile
                140                 145                 150

CTG GAT TCT CGA GAG GAT TAT ATG GGG AAA CAA TCT ATG TAC TCG TTC       532
Leu Asp Ser Arg Glu Asp Tyr Met Gly Lys Gln Ser Met Tyr Ser Phe
            155                 160                 165

ATT GAA TCT CAT TTA CCT GCA GGT TTT AAT GAA TAT GAT TAC ATA CCG       580
Ile Glu Ser His Leu Pro Ala Gly Phe Asn Glu Tyr Asp Tyr Ile Pro
        170                 175                 180

GAT TCA TTT GAC CGC GAA ACA GCA ACA GCA CTT ATA ATG AAT TCA TCG       628
Asp Ser Phe Asp Arg Glu Thr Ala Thr Ala Leu Ile Met Asn Ser Ser
    185                 190                 195

GGA TCT ACT GGA TTG CCC AAG GGA GTT GAG CTT ACT CAC CAA AAT GTG       676
Gly Ser Thr Gly Leu Pro Lys Gly Val Glu Leu Thr His Gln Asn Val
200                 205                 210                 215
```

-continued

```
TGT GTT AGA TTT TCT CAC TGC AGA GAT CCT GTG TTT GGT AAT CAA ATT      724
Cys Val Arg Phe Ser His Cys Arg Asp Pro Val Phe Gly Asn Gln Ile
            220                 225                 230

ATT CCC GAT ACT GCG ATT TTA ACA GTT ATA CCA TTT CAT CAT GGT TTT      772
Ile Pro Asp Thr Ala Ile Leu Thr Val Ile Pro Phe His His Gly Phe
                235                 240                 245

GGA ATG TTT ACA ACA CTA GGA TAT TTA ACG TGT GGA TTT CGT ATT GTG      820
Gly Met Phe Thr Thr Leu Gly Tyr Leu Thr Cys Gly Phe Arg Ile Val
            250                 255                 260

CTT ATG TAT AGA TTT GAA GAG GAA TTA TTT TTA CGA TCA CTT CAA GAT      868
Leu Met Tyr Arg Phe Glu Glu Glu Leu Phe Leu Arg Ser Leu Gln Asp
        265                 270                 275

TAT AAA ATT CAA AGT GCG TTG CTG GTA CCT ACT CTA TTT TCA TTC TTT      916
Tyr Lys Ile Gln Ser Ala Leu Leu Val Pro Thr Leu Phe Ser Phe Phe
280                 285                 290                 295

GCC AAA AGC ACC TTA GTC GAT AAA TAC GAT TTA TCC AAC TTA CAT GAA      964
Ala Lys Ser Thr Leu Val Asp Lys Tyr Asp Leu Ser Asn Leu His Glu
                300                 305                 310

ATT GCG TCT GGT GGA GCT CCC CTC GCG AAA GAA GTT GGA GAA GCT GTA     1012
Ile Ala Ser Gly Gly Ala Pro Leu Ala Lys Glu Val Gly Glu Ala Val
            315                 320                 325

GCA AAA CGT TTT AAG CTG CCG GGA ATA CGA CAA GGG TAT GGA CTT ACT     1060
Ala Lys Arg Phe Lys Leu Pro Gly Ile Arg Gln Gly Tyr Gly Leu Thr
        330                 335                 340

GAA ACT ACC TCA GCT ATT ATA ATT ACA CCA GAA GGG GAT GAT AAA CCA     1108
Glu Thr Thr Ser Ala Ile Ile Ile Thr Pro Glu Gly Asp Asp Lys Pro
345                 350                 355

GGA GCA TGT GGT AAA GTT GTT CCA TTC TTT TCT GCC AAA ATT GTT GAT     1156
Gly Ala Cys Gly Lys Val Val Pro Phe Phe Ser Ala Lys Ile Val Asp
360                 365                 370                 375

CTG GAT ACG GGT AAA ACT TTG GGT GTT AAT CAG AGG GGG GAA TTA TGT     1204
Leu Asp Thr Gly Lys Thr Leu Gly Val Asn Gln Arg Gly Glu Leu Cys
                380                 385                 390

GTG AAA GGC CCA ATG ATA ATG AAG GGT TAC GTA AAC AAC CCA GAA GCA     1252
Val Lys Gly Pro Met Ile Met Lys Gly Tyr Val Asn Asn Pro Glu Ala
            395                 400                 405

ACA AGT GCA TTG ATA GAC AAA GAT GGT TGG TTA CAC TCT GGT GAC ATA     1300
Thr Ser Ala Leu Ile Asp Lys Asp Gly Trp Leu His Ser Gly Asp Ile
        410                 415                 420

GCT TAC TAC GAC AAA GAT GGT CAC TTC TTC ATA GTA GAT CGT TTG AAA     1348
Ala Tyr Tyr Asp Lys Asp Gly His Phe Phe Ile Val Asp Arg Leu Lys
425                 430                 435

TCG TTA ATT AAA TAC AAA GGT TAT CAG GTA CCG CCT GCC GAA TTA GAA     1396
Ser Leu Ile Lys Tyr Lys Gly Tyr Gln Val Pro Pro Ala Glu Leu Glu
440                 445                 450                 455

TCG ATA TTG CTG CAA CAT CCC TTC ATA TTT GAT GCA GGT GTT GCA GGA     1444
Ser Ile Leu Leu Gln His Pro Phe Ile Phe Asp Ala Gly Val Ala Gly
                460                 465                 470

ATT CCC GAC CCA GAT GCC GGT GAA CTT CCT GCA GCC GTT GTT GTC TTA     1492
Ile Pro Asp Pro Asp Ala Gly Glu Leu Pro Ala Ala Val Val Val Leu
            475                 480                 485

GAG GAA GGC AAA ACG ATG ACT GAA CAA GAA GTG ATG GAT TAT GTT GCG     1540
Glu Glu Gly Lys Thr Met Thr Glu Gln Glu Val Met Asp Tyr Val Ala
        490                 495                 500

GGA CAA GTA ACT GCT TCT AAG CGT TTA CGT GGA GGA GTT AAG TTT GTG     1588
Gly Gln Val Thr Ala Ser Lys Arg Leu Arg Gly Gly Val Lys Phe Val
505                 510                 515

GAC GAA GTA CCT AAA GGT CTA ACT GGA AAG ATT GAT GGA AGA AAA ATC     1636
Asp Glu Val Pro Lys Gly Leu Thr Gly Lys Ile Asp Gly Arg Lys Ile
520                 525                 530                 535
```

```
AGG GAG ATC CTT ATG ATG GGA AAA AAA TCC AAA TTG TAATTCCTTC         1682
Arg Glu Ile Leu Met Met Gly Lys Lys Ser Lys Leu
             540                     545

GGTTTACTAT ATTCTAACGA AATTTCTACT ACCATAAACA ATC                    1725
```

(2) INFORMATION FOR SEQ ID NO: 20:

(i) SEQUENCE CHARACTERISTICS:
        (A) LENGTH: 547 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Glu Asp Ala Lys Asn Ile Met His Gly Pro Ala Pro Phe Tyr Pro
 1               5                  10                  15

Leu Glu Asp Gly Thr Ala Gly Glu Gln Leu His Lys Ala Met Lys Arg
             20                  25                  30

Tyr Ala Gln Val Pro Gly Thr Ile Ala Phe Thr Asp Ala His Ala Glu
         35                  40                  45

Val Asn Ile Thr Tyr Ser Glu Tyr Phe Glu Met Ala Cys Arg Leu Ala
     50                  55                  60

Glu Thr Met Lys Arg Tyr Gly Leu Gly Leu Gln His His Ile Ala Val
 65                  70                  75                  80

Cys Ser Glu Asn Ser Leu Gln Phe Phe Met Pro Val Cys Gly Ala Leu
                 85                  90                  95

Phe Ile Gly Val Gly Val Ala Ser Thr Asn Asp Ile Tyr Asn Glu Arg
            100                 105                 110

Glu Leu Tyr Asn Ser Leu Ser Ile Ser Gln Pro Thr Ile Val Ser Cys
        115                 120                 125

Ser Lys Arg Ala Leu Gln Lys Ile Leu Gly Val Gln Lys Lys Leu Pro
130                 135                 140

Ile Ile Gln Lys Ile Val Ile Leu Asp Ser Arg Glu Asp Tyr Met Gly
145                 150                 155                 160

Lys Gln Ser Met Tyr Ser Phe Ile Glu Ser His Leu Pro Ala Gly Phe
                165                 170                 175

Asn Glu Tyr Asp Tyr Ile Pro Asp Ser Phe Asp Arg Glu Thr Ala Thr
            180                 185                 190

Ala Leu Ile Met Asn Ser Ser Gly Ser Thr Gly Leu Pro Lys Gly Val
        195                 200                 205

Glu Leu Thr His Gln Asn Val Cys Val Arg Phe Ser His Cys Arg Asp
210                 215                 220

Pro Val Phe Gly Asn Gln Ile Ile Pro Asp Thr Ala Ile Leu Thr Val
225                 230                 235                 240

Ile Pro Phe His His Gly Phe Gly Met Phe Thr Thr Leu Gly Tyr Leu
                245                 250                 255

Thr Cys Gly Phe Arg Ile Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Val Asp Lys Tyr
    290                 295                 300

Asp Leu Ser Asn Leu His Glu Ile Ala Ser Gly Gly Ala Pro Leu Ala
305                 310                 315                 320
```

```
Lys Glu Val Gly Glu Ala Val Ala Lys Arg Phe Lys Leu Pro Gly Ile
                325                 330                 335

Arg Gln Gly Tyr Gly Leu Thr Glu Thr Thr Ser Ala Ile Ile Ile Thr
            340                 345                 350

Pro Glu Gly Asp Asp Lys Pro Gly Ala Cys Gly Lys Val Val Pro Phe
        355                 360                 365

Phe Ser Ala Lys Ile Val Asp Leu Asp Thr Gly Lys Thr Leu Gly Val
    370                 375                 380

Asn Gln Arg Gly Glu Leu Cys Val Lys Gly Pro Met Ile Met Lys Gly
385                 390                 395                 400

Tyr Val Asn Asn Pro Glu Ala Thr Ser Ala Leu Ile Asp Lys Asp Gly
                405                 410                 415

Trp Leu His Ser Gly Asp Ile Ala Tyr Tyr Asp Lys Asp Gly His Phe
            420                 425                 430

Phe Ile Val Asp Arg Leu Lys Ser Leu Ile Lys Tyr Lys Gly Tyr Gln
        435                 440                 445

Val Pro Pro Ala Glu Leu Glu Ser Ile Leu Leu Gln His Pro Phe Ile
    450                 455                 460

Phe Asp Ala Gly Val Ala Gly Ile Pro Asp Pro Asp Ala Gly Glu Leu
465                 470                 475                 480

Pro Ala Ala Val Val Val Leu Glu Glu Gly Lys Thr Met Thr Glu Gln
                485                 490                 495

Glu Val Met Asp Tyr Val Ala Gly Gln Val Thr Ala Ser Lys Arg Leu
            500                 505                 510

Arg Gly Gly Val Lys Phe Val Asp Glu Val Pro Lys Gly Leu Thr Gly
        515                 520                 525

Lys Ile Asp Gly Arg Lys Ile Arg Glu Ile Leu Met Met Gly Lys Lys
    530                 535                 540

Ser Lys Leu
545

(2) INFORMATION FOR SEQ ID NO: 21:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO: 21:

Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
```

-continued

```
            115                 120                 125
Ser Lys Lys Gly Leu Gln Lys Ile Leu Asn Val Gln Lys Lys Leu Pro
    130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
            195                 200                 205
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
            275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
                500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
    530                 535                 540
```

```
Gly Gly Lys Ser Lys Leu
545                 550
```

What is claimed is:

1. A recombinant mutant luciferase having 70% or more homology to a luciferase of *Photinus pyralis* (SEQ ID NO: 21), *Luciola cruciata* (SEQ ID NO:14), *Luciola lateralis* (SEQ ID NO:16), *Luciola mingrelica* (SEQ ID NO:18) or *Lampyris noctiluca* (SEQ ID NO:20); wherein the amino-acid corresponding to amino acid residue number 245 or 318 in *Photinus pyralis* luciferase has been substituted with respect to the corresponding wild-type amino acid residue such that the $K_m$ for ATP is increased with respect to that of the corresponding non-mutated enzyme.

2. A recombinant mutant luciferase according to claim 1 wherein the amino-acid corresponding to amino acid residue number 245 in *Photinus pyralis* luciferase has been substituted with respect to the corresponding wild-type amino acid residue.

3. A luciferase as claimed in claim 1 wherein the $K_m$ is at least double that of the non-mutated enzyme.

4. A luciferase as claimed in claim 3 wherein the $K_m$ is at least five times higher than that of the non-mutated enzyme.

5. A luciferase as claimed in claim 1 wherein the $K_m$ is of the order of 500 $\mu$m.

6. A luciferase as claimed in claim 1 wherein the $K_m$ is of the order of 1 mM.

7. A luciferase as claimed in claim 1 having a $V_m$ for ATP which is 5–100% of that of the corresponding wild-type.

8. A luciferase as claimed in claim 2 wherein the said amino-acid has been substituted for an uncharged amino acid.

9. A luciferase as claimed in claim 7 wherein the amino-acid has been substituted for Ala, Asn, or Gln.

10. A luciferase as claimed in claim 1 which is derived from *Photinus pyralis* and wherein amino acid residue number 245 has, been substituted.

11. A luciferase as claimed in claim 1 which is derived from *Luciola cruciata* and wherein amino acid residue number 247 has been substituted.

12. A luciferase as claimed in claim 1 that includes one or more mutations capable of conferring one or more of the following properties with respect to a corresponding non-mutated enzyme: improved thermostability; or, altered wavelength of emitted light.

13. A fusion protein comprising a luciferase as claimed in claim 1.

14. A recombinant polynucleotide encoding a luciferase as claimed in claim 1.

15. A replication vector comprising a polynucleotide as claimed in claim 14 further comprising a replication element which permits replication of the vector in a suitable host cell.

16. An expression vector comprising a polynucleotide as claimed in claim 14 further comprising a promoter element which permits expression of said polynucleotide in a suitable host cell.

17. A vector as claimed in claim 16 wherein the promoter element is tissue or organ specific.

18. A host cell containing a vector as claimed in claim 15.

19. A host cell transformed with a vector as claimed in claim 15.

20. A host cell as claimed in claim 19 which also expresses a second luciferase having a lower $K_m$ for ATP.

21. A host cell as claimed in claim 20 wherein the second luciferase is selected from: (a) a recombinant non-mutant luciferase: and (b) a recombinant mutant luciferase having a mutation which is such that the $K_m$ for ATP of the luciferase is decreased with respect to that of the corresponding non-mutated enzyme.

22. A process for producing a luciferase comprising culturing a host cell as claimed in claim 19.

23. A method of assaying the amount of ATP in a material, said method comprising the steps of (a) contacting a recombinant mutant luciferase of claim 1 with the material and luciferin; (b) measuring the intensity of light emitted by the luciferase; and (c) the measurement in step (b) is correlated directly with the amount of ATP in the material.

24. A method according to claim 23 wherein the concentration of the ATP in the material is expected to be between 300 $\mu$m and 6 mM.

25. A method according to claim 23 wherein step (c) is effected by comparison of the measurement obtained in step (b) with a control value.

26. A method as claimed in claim 23 wherein the measurement in step (b) is monitored continuously.

27. A method as claimed in claim 23 wherein the material measured is a cell which forms part of a synapse.

28. A method as claimed in claim 23 wherein the material is a cell and the luciferase is introduced into the cell.

29. A method as claimed in claim 28 wherein the luciferin is introduced into the cell by direct injection.

30. A method as claimed in claim 28 wherein the luciferase is introduced into the cell by transforming the cell with a vector comprising a polynucleotide which encodes a recombinant mutant luciferase.

31. A method of producing a mutant luciferase with an increased Michaelis-Menten constant ($K_m$) for the substrate ATP of a luciferase enzyme having 70% or more homology to luciferase of *Photinus pyralis* (SEQ ID NO: 21), *Luciola cruciata* (SEQ ID NO:14), *Luciola lateralis* (SEQ ID NO:16), *Luciola mingrelica* (SEQ ID NO:18) or *Lampyris noctiluca* (SEQ ID NO:20); said method comprising mutating an amino acid residue of said luciferase corresponding to residue 245 or 318 of *Photinus pyralis* luciferase.

32. A luciferase produced by the method of claim 31.

33. In a luciferase having 70% or more homology to luciferase of *Photinus pyralis* (SEQ ID NO: 21), *Luciola cruciata* (SEQ ID NO:14), *Luciola lateralis* (SEQ ID NO:16), *Luciola mingrelica* (SEQ ID NO:18) or *Lampyris noctiluca* (SEQ ID NO:20); the improvement comprising a mutated amino acid at the amino acid residue corresponding to residue 245 or 318 of *Photinus pyralis* luciferase, wherein said improved luciferase has a $K_m$ for the substrate ATP which is higher than that of the wild type luciferase.

34. A test kit comprising a luciferase as claimed in claim 1 and further comprising one or more of the following (a) a buffer or dry materials for preparing a buffer; (b) two or more measured portions of ATP suitable for preparing standard solutions; (c) luciferin; (d) instructions for carrying out an ATP assay.

* * * * *